(12) United States Patent
Young et al.

(10) Patent No.: US 11,135,289 B2
(45) Date of Patent: Oct. 5, 2021

(54) FUCOIDAN-QUATERNIZED CHITOSAN NANOPARTICLES AND APPLICATION THEREOF

(71) Applicant: National Defense Medical Center, Taipei (TW)

(72) Inventors: Jenn-jong Young, New Taipei (TW); Chuan-Chang Chuang, New Taipei (TW); Meng-Hung Tsai, Taipei (TW); Huey-Fen Shyu, Tainan (TW); Cheng-cheung Chen, Taipei (TW); Kuang-ming Cheng, Taipei (TW); Jyh-Hwa Kau, Taoyuan (TW); Hui-Ju Yen, Taoyuan (TW); Fwu-Long Mi, Taipei (TW)

(73) Assignee: NATIONAL DEFENSE MEDICAL CENTER, Taipei (TW)

( * ) Notice: Subject to any disclaimer, the term of this patent is extended or adjusted under 35 U.S.C. 154(b) by 0 days.

(21) Appl. No.: 16/392,856

(22) Filed: Apr. 24, 2019

(65) Prior Publication Data
US 2020/0338191 A1 Oct. 29, 2020

(51) Int. Cl.
*A61K 39/39* (2006.01)
*A61K 39/00* (2006.01)
*A61K 9/51* (2006.01)

(52) U.S. Cl.
CPC ............ *A61K 39/39* (2013.01); *A61K 9/5161* (2013.01); *A61K 2039/55583* (2013.01)

(58) Field of Classification Search
CPC .... A61K 2039/555; A61K 2039/55505; A61K 2039/55583; A61K 2039/55511; A61K 9/51; A61K 9/5161
See application file for complete search history.

(56) References Cited

U.S. PATENT DOCUMENTS

2016/0222137 A1* 8/2016 Mousa ............... C08B 37/0075

OTHER PUBLICATIONS

Tsai (Tsai, L.-C., et al., Development of mutlifunctional nanoparticles self-assembled from trimethyl chitosan and fucoidan for enhanced oral delivery of insulin, International Journal of Biological Macromolecules 126 (2019) 141-150, available online Dec. 23, 2018).*
Bowman, K., Leong K. W., Chitosan nanoparticles for oral drug and gene delivery, Int J Nanomedicine. Jun. 2006; 1(2): 117-128.*
Hagenaars, N., et al., Relationship between structure and adjuvanticity of N,N,N-trimethyl chitosan (TMC) structural variants in a nasal influenza vaccine, Journal of Controlled Release 140 (2009) 126-133.*
Jenn-Jong Young et al., Preparation of cross-linked hyaluronic acid film using 2-chloro-1-methylpyridinium iodide or water-soluble 1-ethyl-(3,3-dimethylaminopropyl)carbodiimide, J. Biomater. Sci. Polymer Edn, 2004, pp. 767-780, vol. 15, No. 6, Taylor & Francis Group, London, UK.
Ming-Kung Yeh et al., A novel cell support membrane for skin tissue engineering: Gelatin film cross-linked with 2-chloro-1-methylpyndinium iodide, Polymer, Nov. 4, 2010, pp. 996-1003, vol. 52, Elsevier, Amsterdam, Netherlands.
Shu Zhang et al., Curdlan sulfate-O-linked quaternized chitosan nanoparticles: potential adjuvants to improve the immunogenicity of exogenous antigens via intranasal vaccination. International Journal of Nanomedicine, 2018, pp. 2377-2394, vol. 13, Dove Medical Press Limited, Macclesfield, UK.

* cited by examiner

*Primary Examiner* — H. Sarah Park
(74) *Attorney, Agent, or Firm* — Locke Lord LLP; Tim Tingkang Xia, Esq.

(57) ABSTRACT

The present invention relates to fucoidan-quaternized chitosan nanoparticles, an immunogenic composition containing the fucoidan-quatemized chitosan nanoparticles, and a method of delivering an agent to a cell by the fucoidan-quaternized chitosan nanoparticles.

3 Claims, 15 Drawing Sheets

FUCOIDAN-QUATERNIZED CHITOSAN NANOPARTICLES AND APPLICATION THEREOF

BACKGROUND OF THE INVENTION

1. Field of the Invention

The present invention relates to fucoidan-quaternized chitosan nanoparticles and application thereof, especially to fucoidan-quaternized chitosan nanoparticles with opposite surface charges used as nano-carriers and vaccine adjuvants.

2. Description of the Prior Art

CpG ODNs are synthetic Toll-like receptor 9 (TLR9) agonists that have been shown to be potent vaccine adjuvants and can accelerate both the antigen-specific antibody response and the natural killer T-cell response when used in a mixture with vaccines targeting infectious diseases and cancers. They are being developed as a next generation vaccine adjuvant that is expected to confer protection more quickly and require fewer vaccinations. However, CpG ODNs are very expensive as vaccine adjuvant, and the cost could limit their widespread use in vaccine development. Therefore, there is an urgent need to develop new materials used as vaccine adjuvants and carriers for delivering agents to cells.

SUMMARY OF THE INVENTION

In one aspect, the present invention relates to fucoidan-quaternized chitosan nanoparticles. The fucoidan-quaternized chitosan nanoparticles of the present invention comprise 10 to 90% by weight of anionic fucoidan and 90 to 10% by weight of cationic quaternized chitosan salt and are formed via polyelectrolyte complexation (PEC).

In another aspect, the present invention relates to an immunogenic composition, comprising an antigenic substance and a fucoidan-quaternized chitosan nanoparticle of the present invention.

In yet another aspect, the present invention relates to a method of delivering an agent to a cell, comprising administering the cell with a combination of the agent and a fucoidan-quaternized chitosan nanoparticle of the present invention.

These and other aspects will become apparent from the following description of the preferred embodiment taken in conjunction with the following drawings.

BRIEF DESCRIPTION OF THE DRAWINGS

The accompanying drawings illustrate one or more embodiments of the invention and, together with the written description, serve to explain the principles of the invention. Wherever possible, the same reference numbers are used throughout the drawings to refer to the same or like elements of an embodiment.

DETAILED DESCRIPTION OF THE PREFERRED EMBODIMENT

Figure 1:
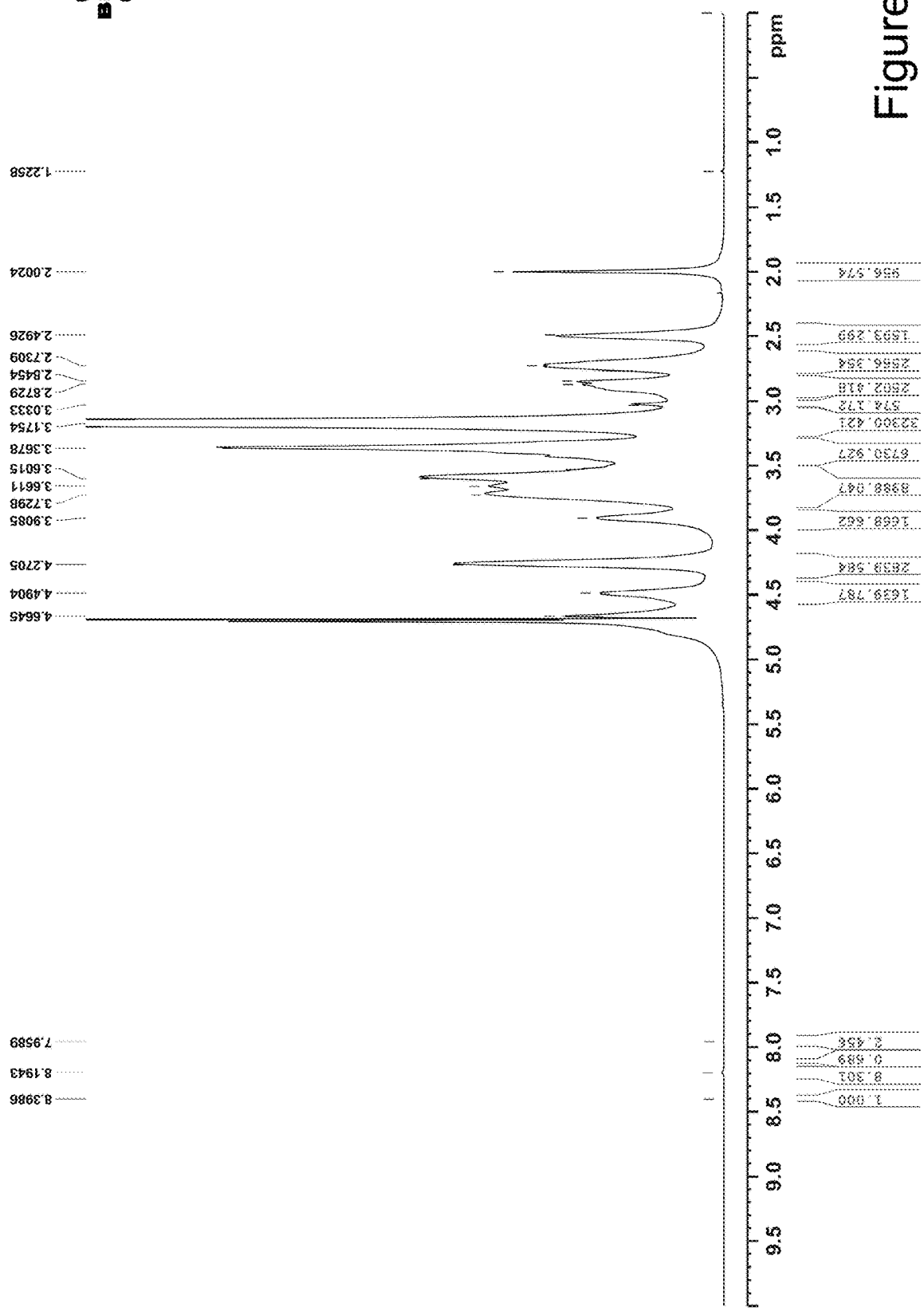
FIG. 1 shows the NMR spectra of N-(2-hydroxy)propyl-3-trimethyl ammonium chitosan chloride (HTCC).

The first aspect of the present invention provides fucoidan-quaternized chitosan nanoparticles. The fucoidan-quaternized chitosan nanoparticles comprise 10 to 90% by weight of anionic fucoidan and 90 to 10% by weight of cationic quaternized chitosan salt. In some embodiments, the fucoidan-quaternized chitosan nanoparticles of the present invention are formed via polyelectrolyte complexation (PEC).

In some embodiments, the fucoidan-quaternized chitosan nanoparticles of the present invention comprise about 10%, 12.5%, 15%, 17.5%, 20%, 22.5%, 25%, 27.5%, 30%, 32.5%, 35%, 37.5%, 40%, 42.5%, 45%, 47.5%, 50%, 52.5%, 55%, 57.5%, 60%, 62.5%, 65%. 67.5%, 70%, 72.5%, 75%, 77.5%, 80%, 82.5%, 85%, 87.5%, or 90% by weight of anionic fucoidan salt and about 90%, 87.5%, 85%, 82.5%, 80%, 77.5%, 75%, 72.5%, 70%, 67.5%, 65%, 62.5%, 60%, 57.5%, 55%, 52.5%, 50%, 47.5%, 45%, 42.5%, 40%, 37.5%, 35%, 32.5%, 30%, 27.5%, 25%, 22.5%, 20%, 17.5%, 15%, 12.5%, or 10% by weight of cationic quaternized chitosan salt, respectively.

In some embodiments, the fucoidan-quaternized chitosan nanoparticles of the present invention have a particle size of no more than about 1000 nm. In some embodiments, the fucoidan-quaternized chitosan nanoparticles of the present invention have a particle size of about 1000 nm, 975 nm, 950 nm, 925 nm, 900 nm, 875 nm, 850 nm, 825 nm, 800 nm, 775 nm, 750 nm, 725 nm, 700 nm, 675 nm, 650 nm, 625 nm, 600 nm, 575 nm, 550 nm, 525 nm, 500 nm, 475 nm, 450 nm, 425 nm, 400 nm, 375 nm, 350 nm, 325 nm, 300 nm, 275 nm, 250 nm, 225 nm, 200 nm, 175 nm, 150 nm, 125 nm, 100 nm, 75 nm, 50 nm, or 25 nm, or even less.

In some embodiments, the fucoidan-quaternized chitosan nanoparticles of the present invention have an absolute value of zeta potential of no less than about 10 mV. In some embodiments, the fucoidan-quaternized chitosan nanoparticles of the present invention have an absolute value of zeta potential of about 10 mV, 12 mV, 14 mV, 16 mV, 18 mV, 20 mV, 22 mV, 24 mV, 26 mV, 28 mV, 30 mV, 32 mV, 34 mV, 36 mV, 38 mV, 40 mV, 42 mV, 44 mV, 46 mV, 48 mV, 50 mV, 52 mV, 54 mV, 56 mV, 58 mV, 60 mV, 62 mV, 64 mV, 66 mV, 68 mV, or 70 mV, or even higher.

In some embodiments, the fucoidan-quaternized chitosan nanoparticles of the present invention comprise 10 to 90% by weight of fucoidan and 90 to 10% by weight of N-(2-hydroxy)propyl-3-trimethyl ammonium chitosan (HTC), and the fucoidan-quaternized chitosan nanoparticles of the present invention are fucoidan-N-[(2-hydroxy-3-trimethyl-ammonium)propyl]chitosan nanoparticles (FUC-HTC-NPs).

In some embodiments, the fucoidan-N-[(2-hydroxy-3-trimethyl-ammonium)-propyl]chitosan nanoparticles (FUC-HTC NPs) have positive charges on the surface of the nanoparticles ((+)-FUC-HTC NPs), and have zeta potential larger than or equal to 10 mV.

In some embodiments, the fucoidan-N-[(2-hydroxy-3-trimethyl-ammonium)propyl]chitosan nanoparticles (FUC-HTC NPs) have negative charges on the surface of the nanoparticle ((−)-FUC-HTC NPs)), and have zeta potential smaller than or equal to −10 mV.

In some embodiments, the fucoidan-quatemized chitosan nanoparticles of the present invention comprise 10 to 90% by weight of fucoidan and 90 to 10% by weight of N,N,N-trimethyl chitosan (TMC), and the fucoidan-quatemized chitosan nanoparticles of the present invention are fucoidan-N,N,N-Trimethyl chitosan nanoparticles (FUC-TMC NPs).

In some embodiments, the fucoidan-N,N,N-Trimethyl chitosan nanoparticles (FUC-TMC NPs) have positive charges on the surface of the nanoparticles ((+)-FUC-TMC NPs), and have zeta potential larger than or equal to 10 mV.

In some embodiments, the fucoidan-N,N,N-Trimethyl chitosan nanoparticles (FUC-TMC NPs) have negative charges on the surface of the nanoparticles ((−)-FUC-TMC NPs), and have zeta potential smaller than or equal to −10 mV.

The second aspect of the present invention provides an immunogenic composition, comprising an antigenic substance and a fucoidan-quatemized chitosan nanoparticle of the present invention.

In some embodiments, the antigenic substance is anonic, and the fucoidan-quatemized chitosan nanoparticle of the present invention is (+)-FUC-HTC NP or (+)-FUC-TMC NP. In some preferable embodiments, the antigenic substance is the antigen of anthrax vaccine adsorbed (AVA) and the fucoidan-quatemized chitosan nanoparticle of the present invention is (+)-FUC-HTC NP. In some preferable embodiments, the antigenic substance is the antigen of anthrax vaccine adsorbed (AVA) and the fucoidan-quatemized chitosan nanoparticle of the present invention is (+)-FUC-TMC NP.

In some embodiments, the antigenic substance is cationic, and the fucoidan-quatemized chitosan nanoparticle of the present invention is (−)-FUC-HTC NP or (−)-FUC-TMC NP.

In some embodiments, the antigenic substance is neutral and the fucoidan-quatemized chitosan nanoparticle of the present invention is FUC-HTC NP or FUC-TMC NP.

The first aspect of the present invention provides a method of delivering an agent to a cell, comprising administering the cell with a combination of the agent and a fucoidan-quatemized chitosan nanoparticle of the present invention.

In some embodiments, the agent is delivered to cytoplasm of the cell, and the fucoidan-quaternized chitosan nanoparticle of the present invention is FUC-HTC NP or FUC-TMC NP.

In some embodiments, the agent is delivered to nucleus of the cell, and the fucoidan-quaternized chitosan nanoparticle of the present invention is FUC-TMC NP.

In some embodiments, the fucoidan-quaternized chitosan nanoparticles of the present invention exhibit no cytotoxicity in fibroblast cells, such as L929 cells, and dendritic cells, such as JAWS II DCs.

In some embodiments, both the positively charged and negatively charged fucoidan-quaternized chitosan nanoparticles of the present invention show excellent uptake efficacy in dendritic cells.

In addition, the fucoidan-quaternized chitosan nanoparticles of the present invention can be easily prepared with high reproductivity via electrostatic interactions between two opposite-charged polyelectrolytes via a simple mixing process. Furthermore, the fucoidan-quaternized chitosan nanoparticles of the present invention are more cost-effective than chemically synthetic adjuvants such as CpG ODNs. In some embodiments, in vivo data show that PA antigen-specific adaptive immune responses significantly increased by the co-administration of AVA with the fucoidan-quaternized chitosan nanoparticles of the present invention (positively charged) in animal models, in which the co-administration elicited higher anti-PA antibody and efficient protection compared to administration of FUC plus AVA, CpG ODN plus AVA or AVA alone. Therefore, the fucoidan-quaternized chitosan nanoparticles of the present invention have been proved to be good nano-carriers and vaccine adjuvant candidates.

Unless otherwise defined, all technical and scientific terms used herein have the same meaning as commonly understood by one of ordinary skill in the art to which this invention pertains. In the case of conflict, the present document, including definitions will control.

As used herein, the term "fucoidan (FUC)" refers to a sulfated fucose-rich polysaccharides having a chemical structure containing a backbone of L-fucose units with a small amount of one or more D-xylose, D-mannose, D-galactose, L-rhamnose, arabinose, glucose, and D-glucuronic acid, among others, depending on the species of brown seaweed from which the fucoidan is extracted. Fucoidan is usually extracted and purified from various species of brown algae and brown seaweed such as, but is not limited to, mozuku (*Cladosiphon okamuranus*), kombu (such as *Laminaria japonica, L. religiosa, L. diabolica, L. ochotensis, L. saccharina, L. angustata, L. longissima, Laminaria coriacea, L. longipedalis, L. cichorioides, Kjellmaniella sculpera, K. gyrata*, and *Arthrothamnus bifidus*), bladderwrack (*Fucus vesiculosus*), serrated wrack (*F. serratus*), wakame (*Undaria pinnatifida*), hijiki (*Sargassum fusiforme*), giant kelp (*Macrocystis pyrifera*), sea lace (*Chorda filum*), and egg wrack (*Ascophyllum nodosum*). Examples of fucoidan structural element are listed below. Examples of fucoidan used in the present invention for preparation of the fucoidan-quaterinized chitosan nanoparticles of the present invention include, but are not limited to, fucoidan from *Arthrothamnus bifidus, Ascophyllum nodosum, Chorda filum, Cladosiphon okamuranus, E. vesiculosus, E. serratus, K. sculpera, K. gyrata, L. japonica, L. religiosa, L. diabolica, L. ochotensis, L. saccharina, L. angustata, L. longissima, Laminaria coriacea, L. longipedalis, L. cichorioides, M. pyrifera, S. fusiforme*, and *U. pinnatifida*.

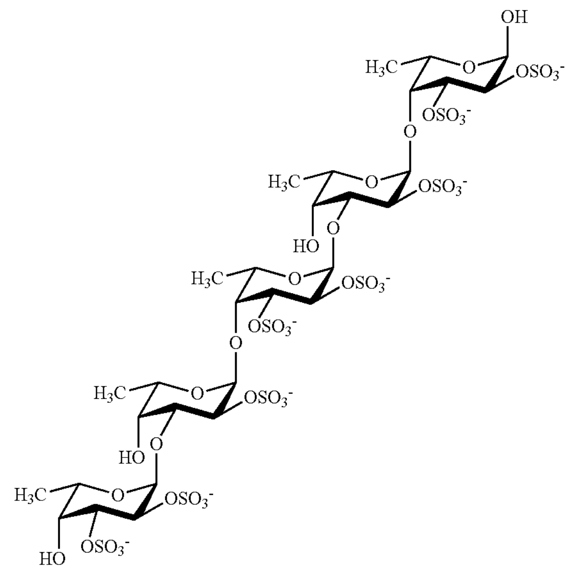

Fucoidan from *Ascoplyllum nodosum*

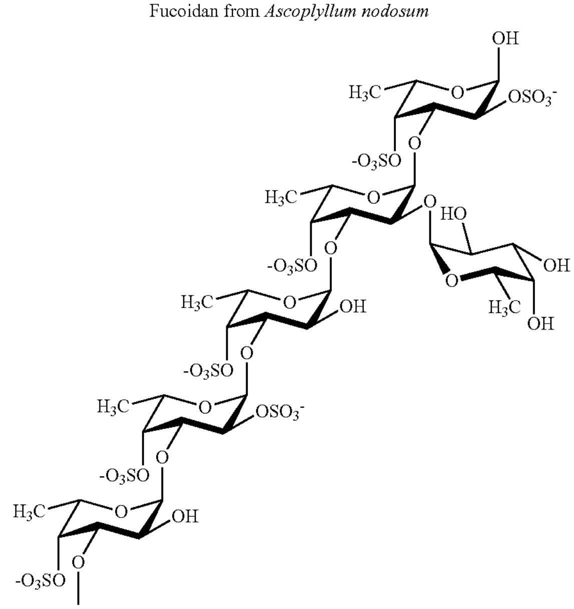

Fucoidan from *Chorda filum*

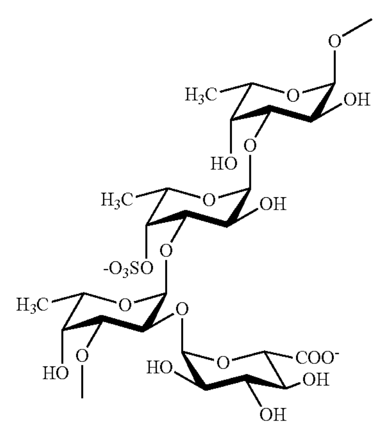

Fucoidan from *Cladosiphon okamuranus*

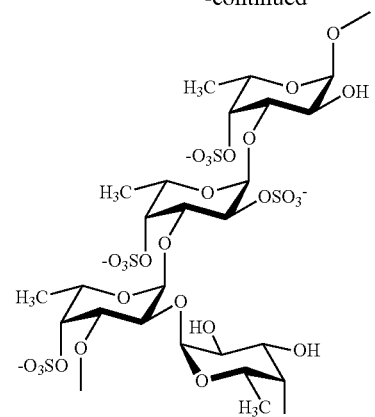

Fucoidan from *Laminaria saccharina*

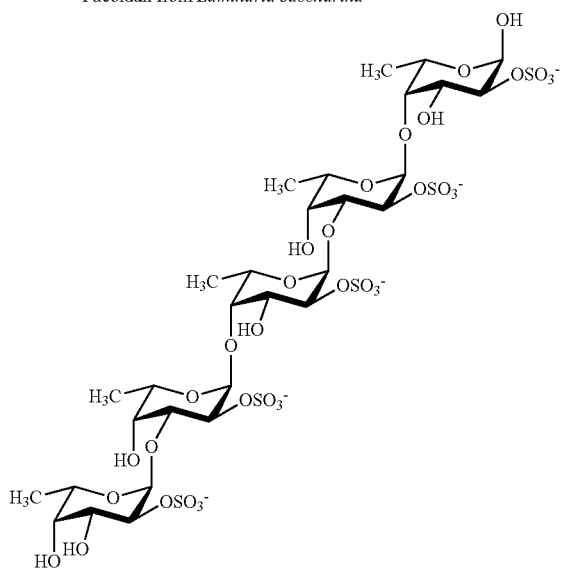

Fucoidan from *Fucus serratus*

As used herein, the term "chitosan" refers to a linear polysaccharide composed of randomly distributed β-(1→4)-linked D-glucosamine (deacetylated unit) and N-acetyl-D-glucosamine (acetylated unit) and having the following chemical structure.

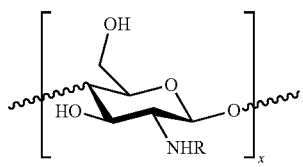

Chitosan
R = H or Ac

As used herein, the term "quaternized chitosan" refers to a chitosan composed of cationic quaternary ammonium salt and complex with different anionic ions. Examples of quaternized chitosan used in the present invention for preparation of the fucoidan-quaternized chitosan nanoparticles of the present invention include, but are not limited to, N-(2-hydroxy)propyl-3-trimethyl ammonium chitosan (HTC) and N,N,N-trimethyl chitosan (TMC).

As used herein, the term "anionic ions" refers to an anion with mono-atom or poly-atom. Examples of anionic ions used in the present invention for preparation of the fucoidan-quaternized chitosan nanoparticles of the present invention include, but are not limited to, fluoride, chloride, bromide, iodide, hydroxide, nitrate, sulfate, phosphate, borate, carbonate, silicate, acetate, oxalate, citrate.

As used herein, the term "degree of quaternization (DQ)" refers to the molar ratio of quaternary ammonium group to the monosaccharide unit of polysaccharide. In some embodiments, the quaternized chitosan salt has a degree of quaternization (DQ) of 10%~200%. In some embodiments, the quaternized chitosan salt has a degree of quaternization (DQ) of about 10%, 15%, 20%, 25%, 30%, 35%, 40%, 45%, 50%, 55%, 60%, 65%, 70%, 75%, 80%, 85%, 90%, 95%, 100%, 105%, 110%, 115%, 120%, 125%, 130%, 135%, 140%, 145%, 150%, 155%, 160%, 165%, 170%, 175%, 180%, 185%, 190%, 195%, or 200%

As used herein, the term "degree of deacetylation (DD)" refers to the molar ratio of D-glucosamine to the monosaccharide unit of chitosan. In some embodiments, the quaternized chitosan salt has a degree of deacetylation (DD) of 10%~99%. In some embodiments, the quaternized chitosan salt has a degree of deacetylation (DD) of about 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

As used herein, the term "N-(2-hydroxy)propyl-3-trimethyl ammonium chitosan (HTC)" refers to a chitosan containing cationic quaternary ammonium salt with the following chemical structure. HTC is a chitosan derivative with permanent cationic charges on the polysaccharide backbone and becomes water-soluble over a wide range of pH values.

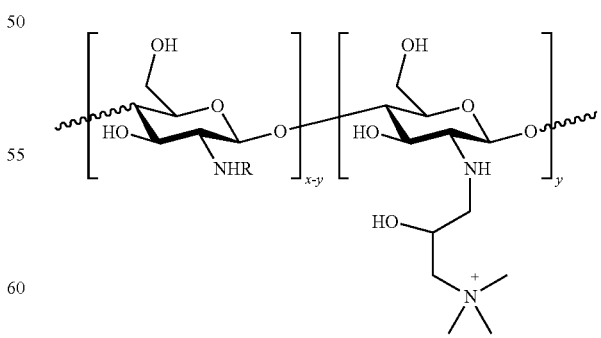

HTCC, R = H or Ac

As used herein, the term "N,N,N-trimethylchitosan (TMC)" refers to a chitosan containing cationic quaternary ammonium salt with the following chemical structure. TMC is a chitosan derivative with permanent cationic charges on the polysaccharide backbone and becomes water-soluble over a wide range of pH values.

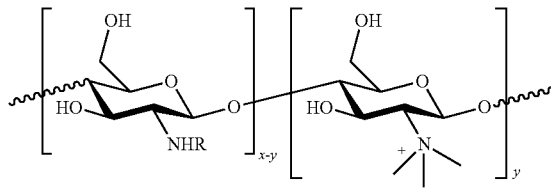

TMC, R = H or Ac

As used herein, the term "polyelectrolyte" refers to a special class of polymeric compounds consisting of net negative or positive charge on the polymer backbone. The interaction between the two oppositely charged polymer results in the formation of a complex, termed as polyelectrolyte complexes. Polyelectrolyte complexes (PECs) are formed due to electrostatic interaction between oppositely charged polyions As used herein, the terms "administer," "administering," and "administration" when used in conjunction with a composition refer to directly or indirectly deliver the composition into or onto a target site. "Administering" a composition may be accomplished by oral, injection, topical administration, or by either method in combination with other known techniques.

As used herein, the term "agent" refers to any molecules that have biological functions and be able to linked with the fucoidan-quaternized chitosan nanoparticles of the present invention. Examples of agents include, but are not limited to, antigens, proteins, antibodies, heptanes, drugs, organic nanoparticles, inorganic nanoparticles, metal nanoparticles, magnetic nanoparticles, quantum dots, carbon nanotubes, graphenes, graphene oxides, dyes or a combination thereof.

As used herein, the term "antigenic substance" refers to a substance that stimulates the production of an antibody when introduced into a living creature. Antigenic substance includes, but is not limited to, DNA, RNA, plasmid, gene, aptamer, peptide, protein, protein fragment, antibody, toxin, bacteria, virus or a combination thereof.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

As used herein, the singular forms "a", "an", and "the" include plural referents unless the context clearly dictates otherwise. Thus, for example, reference to "a component" includes a plurality of such components and equivalents thereof known to those skilled in the art.

The present invention is described in more detail in the following illustrative examples. Although the examples may represent only selected embodiments of the invention, it should be understood that the following examples are illustrative and not limiting.

EXAMPLES

Example 1

Preparation of fucoidan-N-[(2-hydroxy-3-trimethylammonium)propyl]chitosan chloride nanoparticles (FUC-HTCC NPs)

Step 1-1: Synthesis of N-(2-hydroxy)propyl-3-trimethyl ammonium chitosan chloride (HTCC)

Chitosan (CS) (viscosity: 3.6 mPa·s [5 g/L]; degree of deacetylation: 93.8%; Wako Pure Chemical Industries, Ltd., Osaka, Japan) was suspended in milli-Q water at 80° C. Glycidyltrimethylammonium chloride (GTMAC) (Sigma-Aldrich, St. Louis, Mo., USA) was dissolved in an aqueous solution and added dropwise to the CS suspension with continuous stirring. The molar ratio of GTMAC to the amino groups of CS was 4. After reacting at 80° C. for 20 hours, the resulting turbid and yellowish reaction solution was cooled to room temperature and poured into cold acetone (Merck, Darmstadt, Germany). After washing with acetone and methanol (Merck, Darmstadt, Germany), the precipitated product was re-dissolved in water and centrifuged (10,000×g, 20 minutes) to remove the undissolved portion. The clear supernatant was then poured into absolute ethanol (Merck, Darmstadt, Germany) with continuous stirring, and the white precipitate was collected by centrifugation (10,000×g, 10 mins). To obtain purified HTCC, the product was dialyzed (Slide-A-Lyzer® Dialysis Cassette G2, 2000 MWCO, 70 mL capacity) against water for 3 days and lyophilized. The structure of the HTCC was determined by Fourier transform infrared (FTIR) spectroscopy and proton nuclear magnetic resonance ($^1$H-NMR) spectroscopy. The degree of quaternization (DQ) was determined by $^1$H-NMR or by titrating the chloride ions with aqueous $AgNO_3$ and monitoring the solution conductivities.

Results

The DQ of HTCC was measured by conductometric titration of chloride ions. DQ is defined as the molar ratio of bonded GTMAC per molar of glucosamine calculated from the original mass of chitosan and its degree of deacetylation (DD). The formula to determine the DQ of HTCC is as following equation:

$$DS = \frac{V \times c / 1000}{C \times c / 1000 + (W - V \times c \times 314 / 1000) / 162} \times \frac{1}{DD} \times 100\%$$

V (ml) is the volume of $AgNO_3$ solution calculated from the inflection point where the conductivity of the solution is lowest when adding the $AgNO_3$ solution stepwise, c (mole/l) is the concentration of $AgNO_3$ solution, W (g) is the mass of HTCC, and DD is the degree of deacetylation of chitosan. Quaternary glucosamine has a molar mass of 314, and glucosamine has a molar mass of 162.

Dried HTCC (20 mg) was dissolved in 1% (v/v) AcOH (100 ml) and conductometrically titrated with $AgNO_3$ solution (0.01 mole/l). Solution conductivities were monitored with a conductivity meter with a platinum black electrode.

The degree of quaternization (DQ) can also be estimated by $^1$H-NMR (as shown in FIG. 1), and was calculated as following equation:

$$DQ = ([N-(CH_3)_3]/[COCH_3]) \times 1/3 \times (1-\% \ DD)$$

where % DQ is the degree of quaternization as a percentage, % DD is the degree of deacetylation, [N—(CH$_3$)$_3$] is the integral of the singlet peak at 3.2 ppm from the methy proton (9H) of the trimethylammonium chloride, and [COCH$_3$] is the integral of the singlet peak at 2.0 ppm from the acetyl group of the N-acetyl-glucosamine residue. The % DQ obtained from $^1$H-NMR spectra of HTCC was 69.8%, and the % DQ calculated by titration was 71.2%.

Step 1-2: Preparation of fucoidan-N-[(2-hydroxy-3-trimethyl-ammonium)-propyl]chitosan chloride nanoparticles (FUC-HTCC NPs)

Positively (+) and negatively surface-charged (−)-FUC-HTCC NPs were prepared via polyelectrolyte complexation (PEC) by varying the mass ratio of fucoidan (FUC) and HTCC. Anionic polyelectrolyte FUC (from *Fucus vesiculosus*) (Sigma-Aldrich, St. Louis, Mo., USA) was mixed with cationic polyelectrolyte HTCC (product of Step 1-1) at different FUC/HTCC weight ratios (1/9, 2/8, 2.5/7.5, 3.25/6.75, 4/6, 4.5/5.5, 4.75/5.25, 5/5, 5.25/4.75, 5.5/4.5, 6/4, 6.75/3.25, 7.5/2.5, 8/2, and 9/1) with a total polysaccharides concentration (TPC) of 4 mg/mL. The HTCC solution was added dropwise to the FUC solutions or in reverse order. The obtained particles were further analyzed for their yields, size, zeta potential, and turbidity in Example 3.

Example 2

Preparation of fucoidan-N,N,N-Trimethyl chitosan nanoparticles (FUC-TMC NPs)

Step 2-1: Synthesis of N,N,N-Trimethyl chitosan iodide (TMCI) and N,N,N-Trimethyl chitosan chloride (TMCC)

Twelve (12) g chitosan (CS), 28.8 g sodium iodide (Sigma-Aldrich, St. Louis, Mo., USA), and 66 mL 15% aqueous sodium hydroxide (Merck, Darmstadt, Germany) were mixed in 250 mL N-methylpyrrolidinone in a 60° C. water bath. Then, 69 mL methyl iodide (Merck, Darmstadt, Germany) was added, and the reaction was carried out with a Liebig's condenser for 90 minutes. The polymer was collected via precipitation with ethanol and thereafter isolated via centrifugation. The centrifuged product was washed with acetone on a glass filter and dried under vacuum.

The polymer was then mixed with 28.8 g sodium iodide and 66 mL 15% sodium hydroxide in 250 mL N-methylpyrrolidinone at 60° C. Methyl iodide (42 mL) was added to the mixture with rapid stirring, and the reaction was carried out with a Liebig's condenser for 60 minutes. An additional 12 mL methyl iodide and 3.6 g sodium hydroxide pellets were added, and the stirring continued for 1 hour. The product N,N,N-Trimethyl chitosan iodide (TMCI) was precipitated, washed, and dried as described above.

For ion-exchange, the products prepared above were dissolved in 240 mL 10% (w/v) sodium chloride solution (to exchange the iodide ion with chloride) and precipitated with ethanol. The products were repeatedly dissolved in 240 mL water and precipitated with ethanol to remove the remaining sodium chloride. The final products N,N,N-Trimethyl chitosan chloride (TMCC) were dried in a vacuum chamber for at least 12 hours before further characterization.

To determine the degree of quaternization of the TMC polymers, $^1$H nuclear magnetic resonance (NMR) spectra with an NMR spectrometer (AV-500, Bruker, Switzerland) was obtained by dissolving samples of the polymers in deuterium oxide at 80° C. with suppression of the water peak.

Results

Figure 2:
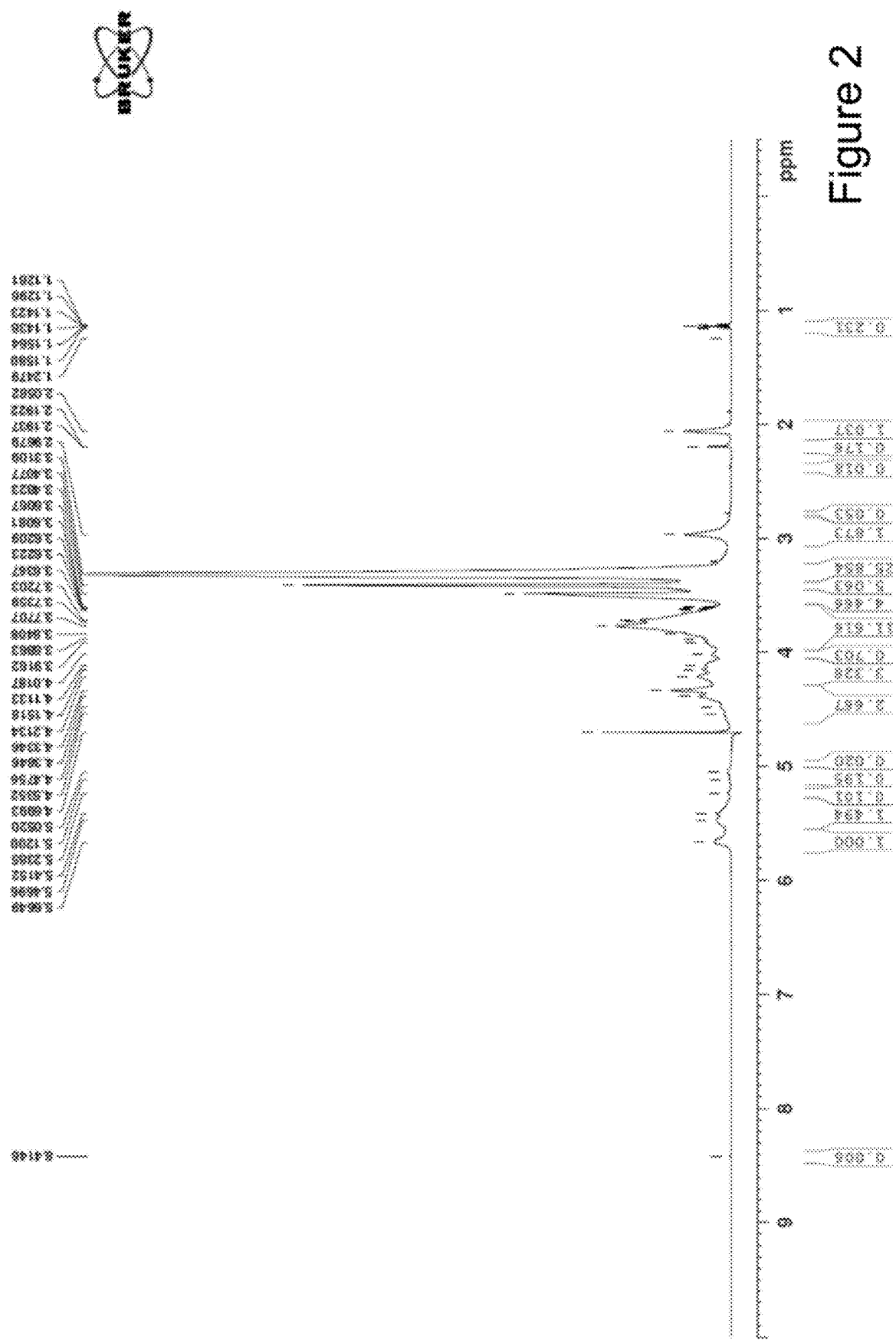
FIG. 2 shows the NMR spectra of N,N,N-trimethyl chitosan chloride (TMCC).

The degree of quaternization was calculated with $^1$H-NMR data according to the following equation.

$$DQ=([N—(CH_3)_3]/[COCH_3])\times 1/3\times(1-\% \text{ DD})$$

where % DQ is the degree of quaternization as a percentage, % DD is the degree of deacetylation, [N—(CH$_3$)$_3$] is the integral of the singlet peak at 3.2 ppm from the methy proton (9H) of the trimethylammonium chloride, and [COCH$_3$] is the integral of the singlet peak at 2.0 ppm from the acetyl group of the N-acetyl-glucosamine residue. The % DQ obtained from $^1$H-NMR spectra of TMC was 52%, (as shown in FIG. 2).

Step 2-2: Preparation of fucoidan-N,N,N-Trimethylchitosan chloride nanoparticles (FUC-TMCC NPs)

Positively (+) or negatively-charged (−)-FUC-TMCC NPs were prepared based on the PEC method of anionic polyelectrolyte FUC with cationic polyelectrolyte TMCC. Preliminary experiments were performed in order to determine the formation zones of positively and negatively charged nanoparticles at different FUC/TMCC weight ratios (9, 4, 3, 2.07, 1.5, 1.22, 1.1, 1, 0.91, 0.82, 0.67, 0.48, 0.33, 0.25, and 0.11) with a total polysaccharides concentration (TPC) of 4 mg/mL. The TMCC solution was added dropwise to the FUC solutions or in reverse order. The particle size, zeta potential, and turbidity were measured at the different weight ratios of FUC/TMCC in order to determine the formation zone of NP suspension.

The obtained particles were further analyzed for their yields, size, zeta potential, and turbidity in Example 3.

Example 3

Characterization of fucoidan-N-[(2-hydroxy-3-trimethyl-ammonium)-propyl]chitosan chloride nanoparticles (FUC-HTCC NPs) and fucoidan-N,N,N-Trimethylchitosan chloride nanoparticles (FUC-TMCC NPs)

1. Formation yields, particle sizes, and surface charge of FUC-HTCC NPs and FUC-TMCC NPs The formation yields of FUC-HTCC NPs and FUC-TMCC NPs at different FUC/HTCC or FUC/TMCC weight ratios were calculated according to the following equation:

$$\text{Yield (\%)}=W_d/(TPC\times V)\times 100$$

where TPC is the total polysaccharide concentration, V is the volume of NPs suspension, TPC×V is the total amount of polysaccharides applied, and $W_d$ is the weight of the dry NPs.

The particle sizes of FUC-HTCC NPs and FUC-TMCC NPs were characterized by photon correlation spectroscopy (Zetasizer Nano-ZS; Malvern Instruments, UK). All measurements were performed at a wavelength of 633 nm at room temperature with a detection angle of 173°. Raw data were subsequently correlated to the mean hydrodynamic size by cumulant analysis (Z-average mean).

The Zeta potentials of all NPs were analyzed using laser doppler anemometry (Zetasizer Nano-ZS; Malvern Instruments, UK). All samples were run in triplicate, and the mean averages and standard deviations (SD) were calculated.

The turbidity of NP suspension was estimated via the transmittance of solution. The transmittance of NP suspension at 600 nm was examined in disposable 1.5-mL plastic cuvettes and recorded on a PerkinElmer Lambda 35 spectrophotometer (Waltham, Mass., USA).

Results a. FUC and HTCC composites can produce NPs with positive or negative charges FIG. 3 and Table 1 show the particle size, zeta potential, formation yield, and solution transmittance of the FUC-HTCC composite at different mass ratios of FUC/HTCC. The data indicate that FUC and HTCC composites can produce NPs with positive or negative charges by simple changing the mass ratios of anionic and cationic polyelectrolytes.

Figure 3:
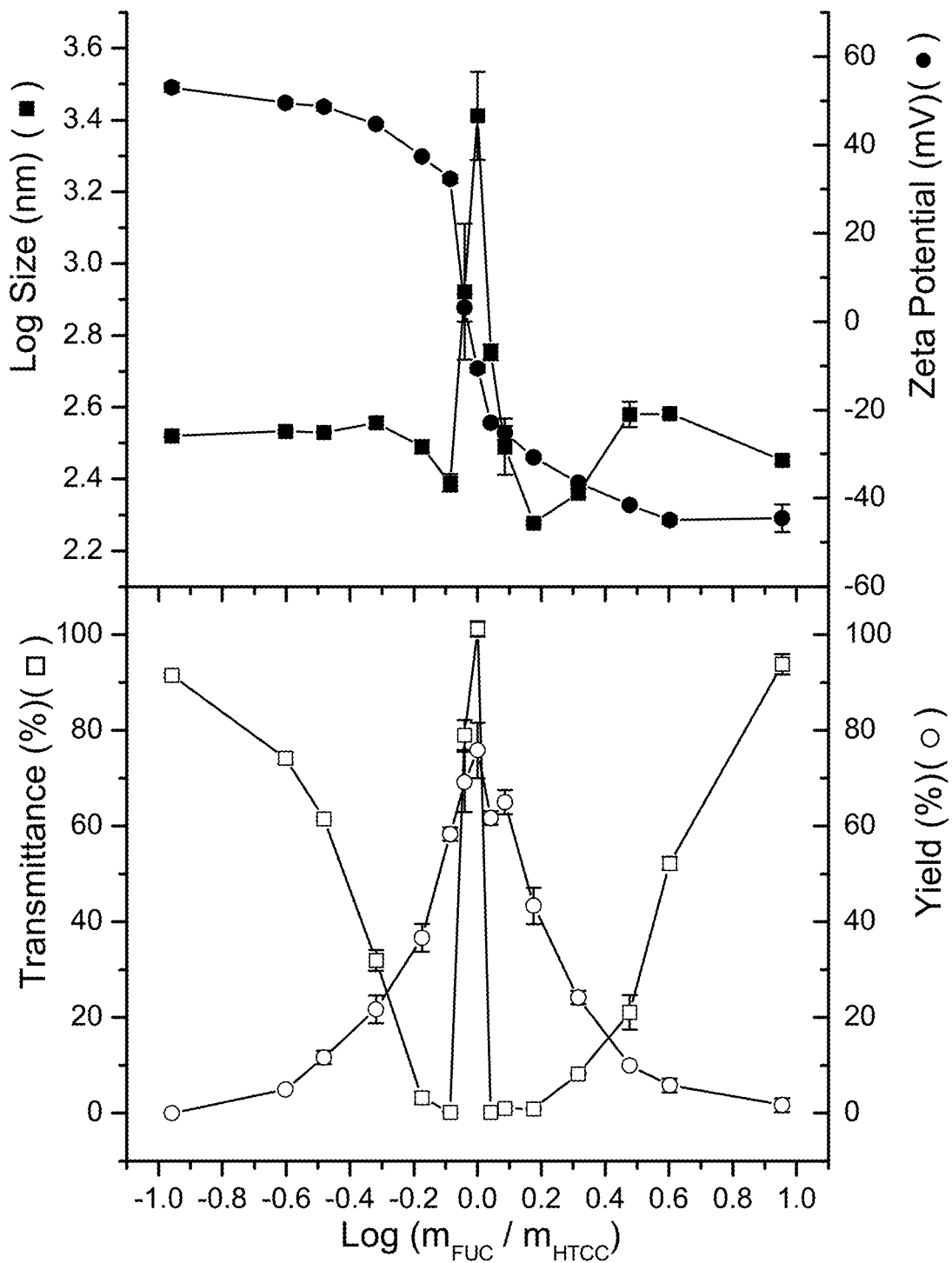
FIG. 3 shows the effect of the mass ratio of fucoidan (FUC)/N-(2-hydroxy)propyl-3-trimethyl ammonium chitosan chloride (HTCC) on particle size (■), zeta potential (●), solution transmittance (□), and formation yield (○). Total polysaccharide concentration (TPC) is 4 mg/mL.

From the particle size, measured via dynamic light scattering (DLS) methods, the NPs aggregated at the mass ratios of FUC and HTCC ranged between 0.82 (4.5/5.5) and 1.22 (5.5/4.5). Moreover, from both particles size and zeta potential, (+)-NPs formed at the mass ratios range of FUC/HTCC less than or equal to 0.82, and (−)-NPs formed at the mass ratios range of FUC/HTCC larger than or equal to 1.22. At the range between 0.82 and 1.22, the absolute values of zeta potentials below 25 mV and the particles size and solution transmittance increased, which represent aggregates or agglomerates formed. FIG. 3 also indicates that the formation yields of NPs (or aggregates) increased as the mass ratios of FUC/HTCC grew closer to the aggregation point and reached a maximum at the aggregation point (zeta potential equal to zero).

TABLE 1

Effect of the mass ratio of fucoidan (FUC)/HTCC on particle size, zeta potential ($\zeta$), solution transmittance, and formation yield.

| FUC/HTCC | Mass Ratio | Size* (nm) | $\zeta$** (mV) | Transmittance (%) | Yield (%) |
|---|---|---|---|---|---|
| 1/9 | 0.11 | 331.0 ± 3.6 | 53.0 ± 1.0 | 91.5 ± 0.5 | 0.0 ± 0.0 |
| 2/8 | 0.25 | 341.0 ± 2.9 | 49.5 ± 0.7 | 74.2 ± 1.2 | 5.0 ± 0.0 |
| 2.5/7.5 | 0.33 | 339.1 ± 1.2 | 48.6 ± 0.9 | 61.5 ± 0.4 | 11.7 ± 1.4 |
| 3.25/6.75 | 0.48 | 360.6 ± 12.2 | 44.7 ± 0.5 | 31.9 ± 2.2 | 21.7 ± 2.9 |
| 4/6 | 0.67 | 308.9 ± 12.9 | 37.4 ± 0.2 | 3.2 ± 1.3 | 36.7 ± 2.9 |
| 4.5/5.5 | 0.82 | 245.3 ± 13.1 | 32.3 ± 0.9 | 0.2 ± 0.1 | 58.3 ± 1.4 |
| 4.75/5.25 | 0.91 | 888.9 ± 376.8 | 3.1 ± 3.1 | 79.0 ± 3.2 | 69.2 ± 6.3 |
| 5/5 | 1 | 2655.3 ± 798.1 | −10.6 ± 0.9 | 101.2 ± 1.6 | 75.8 ± 5.8 |
| 5.25/4.75 | 1.1 | 566.2 ± 28.2 | −22.9 ± 0.4 | 0.2 ± 0.0 | 61.7 ± 1.4 |
| 5.5/4.5 | 1.22 | 312.3 ± 58.8 | −25.2 ± 1.5 | 1.0 ± 0.5 | 65.0 ± 2.5 |
| 6/4 | 1.5 | 189.4 ± 2.7 | −30.7 ± 0.6 | 0.9 ± 0.1 | 43.3 ± 3.8 |
| 6.75/3.25 | 2.07 | 229.7 ± 6.0 | −36.4 ± 0.5 | 8.2 ± 0.2 | 24.2 ± 1.4 |
| 7.5/2.5 | 3 | 380.7 ± 30.7 | −41.5 ± 0.5 | 21.1 ± 3.6 | 10.0 ± 0.0 |
| 8/2 | 4 | 382.7 ± 8.9 | −44.9 ± 0.9 | 52.2 ± 1.4 | 5.8 ± 1.4 |
| 9/1 | 9 | 283.4 ± 7.7 | −44.5 ± 3.1 | 93.8 ± 2.1 | 1.7 ± 1.4 |

*Size measured using the dynamic light scattering method.
**Zeta potential ($\zeta$) measured using the laser Doppler anemometry method.

Table 2 shows that the particle size and the absolute value of zeta potential in re-suspension solution were only marginally larger than in the as-prepared solution, which suggests that both (+)-NPs and (−)-NP can re-suspend well in aqueous after centrifugation. Both NPs, with an absolute value of zeta potential larger than 25 mV, were able to stabilize in as-prepared solution or re-suspension solution for 30 days without aggregation.

TABLE 2

Stability of (+)-FUC-HTCC NPs and (−)-FUC-HTCC NPs stored in as-prepared solution or re-dispersion solution at 4° C. for 30 days.

| FUC/HTCC Mass Ratio | NPs | Day 1 | | Day 30 | |
|---|---|---|---|---|---|
| | | Size (nm) | $\zeta$ (mV) | Size (nm) | $\zeta$ (mV) |
| 0.82 | AS* | 275.0 ± 2.4 | 24.2 ± 0.4 | 251.5 ± 4.8 | 26.0 ± 0.4 |
| 1.5 | AS* | 206.7 ± 1.9 | −25.5 ± 0.9 | 179.3 ± 1.9 | −28.5 ± 0.9 |
| 0.82 | RE** | 369.9 ± 10.2 | 33.9 ± 0.8 | 403.1 ± 5.6 | 37.3 ± 0.3 |
| 1.5 | RE** | 353.9 ± 8.0 | −40.2 ± 1.0 | 261.9 ± 4.2 | −31.7 ± 2.4 |

*AS: As-prepared NPs
**RE: NPs re-dispersed in water after centrifuge (3,000 × g, 30 minutes)

b. FUC and TMCC composites can produce NPs with positive or negative charges FIG. 4 and Table 3 show the particle size, zeta potential, formation yield, and solution transmittance of the FUC-TMCC composite at different mass ratios of FUC/TMCC. The data indicate that FUC and TMCC composites can produce NPs with positive or negative charges by simple changing the mass ratios of anionic and cationic polyelectrolytes.

Figure 4:
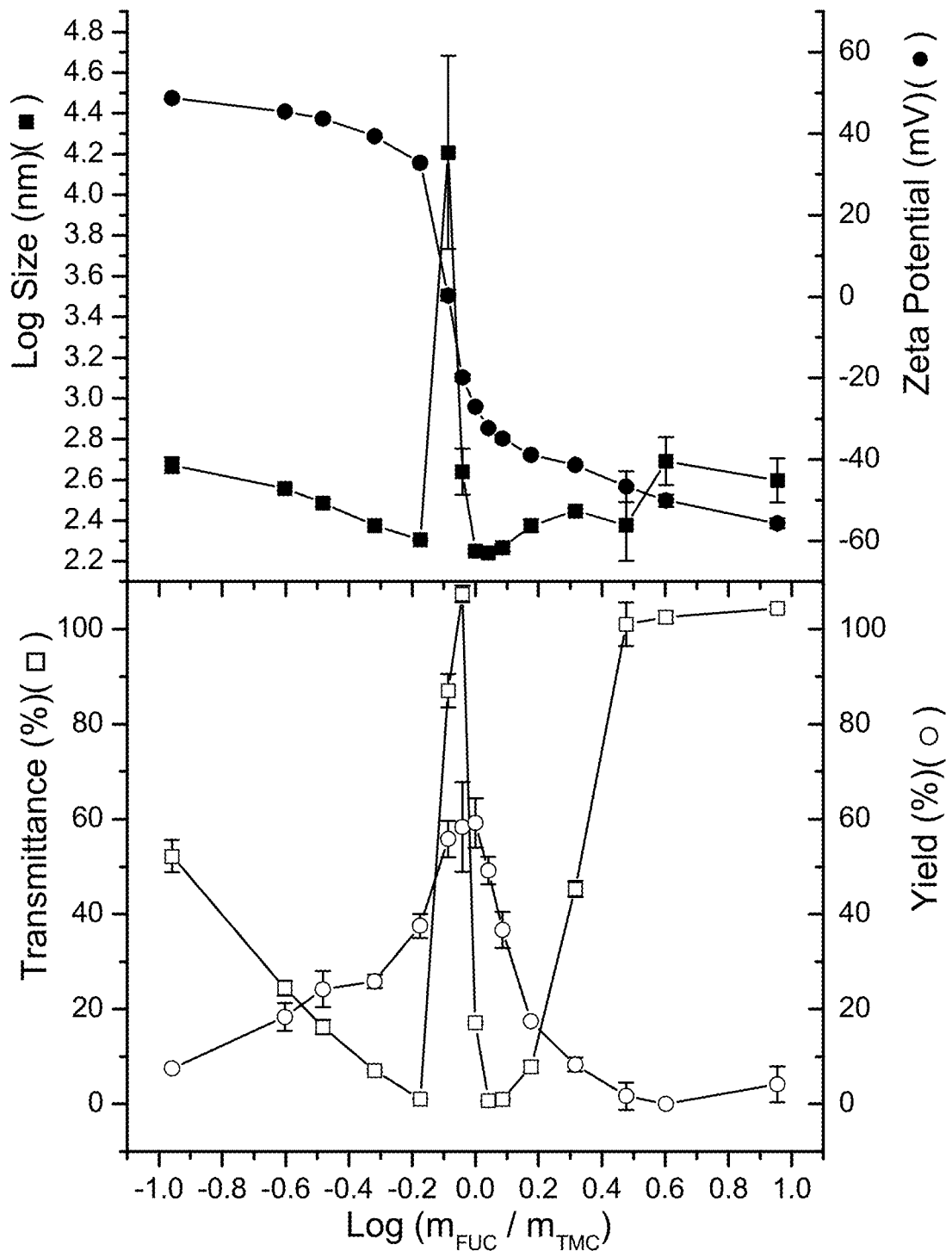
FIG. 4 shows the effect of the mass ratio of fucoidan (FUC)/N,N,N-trimethyl chitosan chloride (TMCC) on particle size (■), zeta potential (●), solution transmittance (□), and formation yield (○). Total polysaccharide concentration (TPC) is 4 mg/mL.

From the particle size, measured via dynamic light scattering (DLS) methods, the NPs aggregated at the mass ratios of FUC and TMCC ranged between 0.67 and 1. Moreover, from both particles size and zeta potential, (+)-NPs formed at the mass ratios range of FUC/TMCC less than or equal to 0.67, and (−)-NPs formed at the mass ratios range of FUC/TMCC larger than or equal to 1. At the range between 0.67 and 1, the absolute values of zeta potentials below 25 mV and the particles size and solution transmittance increased, which represent aggregates or agglomerates formed. FIG. 4 also indicates that the formation yields of NPs (or aggregates) increased as the mass ratios of FUC/TMCC grew closer to the aggregation point and reached a maximum at the aggregation point (zeta potential equal to zero).

TABLE 3

The effect of mass ratio of fucoidan (FUC)/TMCC on particle size, zeta potential ($\zeta$), solution transmittance and formation yield.

| FUC/TMCC | Mass Ratio | Size* (nm) | $\zeta$** (mV) | Transmittance (%) | Yield (%) |
|---|---|---|---|---|---|
| 1/9 | 0.11 | 471.6 ± 40.4 | 48.7 ± 0.3 | 52.2 ± 3.4 | 7.5 ± 0.0 |
| 2/8 | 0.25 | 362.7 ± 11.1 | 45.4 ± 0.2 | 24.4 ± 1.6 | 18.3 ± 2.9 |
| 2.5/7.5 | 0.33 | 306.4 ± 12.5 | 43.7 ± 0.5 | 16.2 ± 1.5 | 24.2 ± 3.8 |
| 3.25/6.75 | 0.48 | 236.9 ± 0.2 | 39.4 ± 0.4 | 7.1 ± 0.4 | 25.8 ± 1.4 |
| 4/6 | 0.67 | 202.4 ± 2.1 | 32.8 ± 0.3 | 1.1 ± 0.1 | 37.5 ± 2.5 |
| 4.5/5.5 | 0.82 | 21927 ± 15887 | 0.3 ± 1.3 | 87.0 ± 3.5 | 55.8 ± 3.8 |
| 4.75/5.25 | 0.91 | 312.4 ± 73.1 | −19.5 ± 2.0 | 107.4 ± 1.7 | 58.3 ± 9.5 |
| 5/5 | 1 | 177.3 ± 4.3 | −27.1 ± 0.2 | 17.1 ± 0.3 | 59.2 ± 5.2 |
| 5.25/4.75 | 1.1 | 174.0 ± 3.1 | −32.3 ± 0.3 | 0.7 ± 0.1 | 49.2 ± 2.9 |
| 5.5/4.5 | 1.22 | 184.5 ± 7.9 | −34.9 ± 0.8 | 1.0 ± 0.2 | 36.7 ± 3.8 |
| 6/4 | 1.5 | 238.3 ± 17.3 | −38.9 ± 0.4 | 7.9 ± 1.2 | 17.5 ± 0.0 |
| 6.75/3.25 | 2.07 | 280.3 ± 8.4 | −41.3 ± 0.6 | 45.3 ± 1.7 | 8.3 ± 1.4 |
| 7.5/2.5 | 3 | 251.9 ± 96.1 | −46.7 ± 3.8 | 101.0 ± 4.6 | 1.7 ± 2.9 |
| 8/2 | 4 | 503.4 ± 141.1 | −50.1 ± 1.5 | 102.5 ± 1.3 | 0.0 ± 0.0 |
| 9/1 | 9 | 403.6 ± 104.6 | −55.7 ± 1.2 | 104.4 ± 0.7 | 4.2 ± 3.8 |

*Size measured using the dynamic light scattering method.
**Zeta potential ($\zeta$) measured using the laser Doppler anemometry method.

Table 4 shows that the particle size and the absolute value of zeta potential in re-suspension solution were only marginally larger than in the as-prepared solution, which suggests that both (+)-NPs and (−)-NP can re-suspend well in aqueous after centrifugation. Both NPs, with an absolute value of zeta potential larger than 25 mV, were able to stabilize in as-prepared solution or re-suspension solution for 30 days without aggregation.

TABLE 4

Stability of (+)-FUC-TMCC NPs and (−)-FUC-TMCC NPs stored as as-prepared solution or re-dispersion solution at 4° C. for 30 days.

| FUC/TMCC Mass Ratio | NPs | Day 1 | | Day 30 | |
|---|---|---|---|---|---|
| | | Size (nm) | $\zeta$ (mV) | Size (nm) | $\zeta$ (mV) |
| 0.67 | AS* | 231.1 ± 4.8 | 23.6 ± 0.7 | 204.0 ± 2.7 | 25.4 ± 0.3 |
| 1.11 | AS* | 200.8 ± 19.5 | −18.6 ± 0.6 | 1159 ± 683 | −19.0 ± 0.4 |
| 0.67 | RE** | 300.9 ± 9.7 | 35.0 ± 1.1 | 279.9 ± 7.1 | 35.1 ± 0.9 |
| 1.11 | RE** | 467.6 ± 14.0 | −30.1 ± 1.7 | 403.4 ± 110.1 | −22.9 ± 1.7 |

*AS: As-prepared
**RE: Re-dispersed in water after centrifuge (5,000 × g, 30 minutes)

2. Fourier transform-infrared (FTIR) spectra of FUC-HTCC NPs and FUC-TMCC NPs NPs were separated from suspension by centrifugation (Model 3740; Kubota Corporation, Tokyo, Japan) at 20,000×g and 4° C. for 30 minutes, and were then dried using a freeze dryer. The Fourier transform-infrared (FTIR) spectra of FUC, HTCC, FUC-HTCC NPs, TMCC, and FUC-TMCC NPs were taken with KBr pellets on a PerkinElmer Spectrum One FTIR (Waltham, Mass., USA).

NP morphology was examined using a Hitachi HT-7700 transmission electron microscope (Minato-ku, Tokyo, Japan). A typical method for preparation of TEM samples was as follows: one drop of FUC-HTCC NP or FUC-TMCC NP suspension (re-suspended in water from the pellet after centrifugation) was deposited on a 200-mesh Formvar/carbon-coated copper grid, and excess solution was removed by wicking with filter paper to avoid particle aggregation. Samples were stained with 2% phosphotungstic acid and dried at room temperature.

Results a. Characterization of FUC-HTCC NPs

Figure 5A:
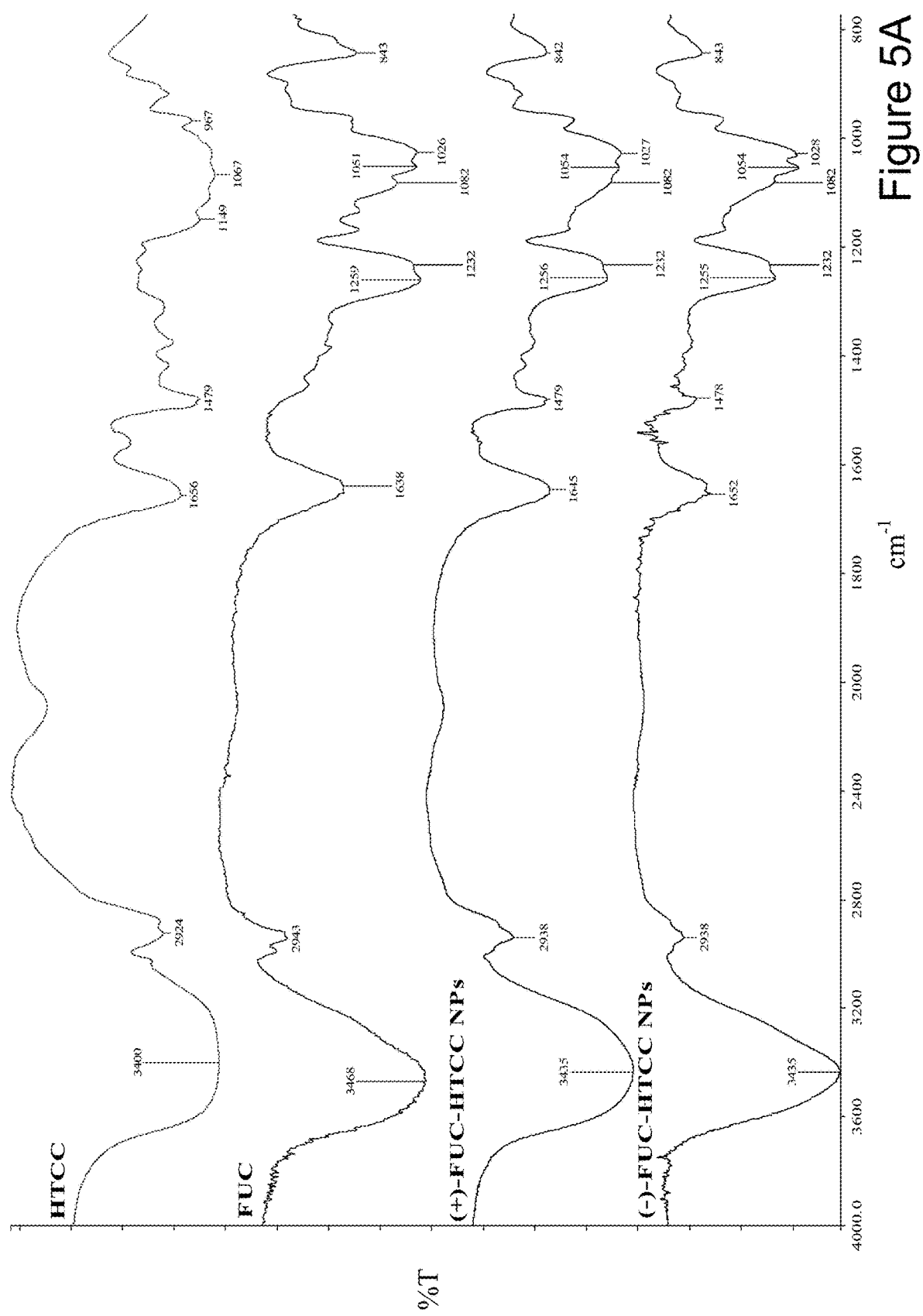
FIGS. 5A-C show the characteristics of fucoidan-N-[(2-hydroxy-3-trimethyl-ammonium)-propyl]chitosan chloride nanoparticles (FUC-HTCC NPs): Fourier transform infrared spectra of HTCC, FUC, (+)-FUC-HTCC NPs, and (−)-FUC-HTCC NPs (FIG. 5A), and transmission electron microscopy imaging of re-suspended (+)-FUC-HTCC NPs (FIG. 5B) and (−)-FUC-HTCC NPs (FIG. 5C) after centrifugal purification.

In FIG. 5A, the FTIR spectrum of FUC contains characteristic peaks at 3468 $cm^{-1}$ (O—H stretch), 2943 $cm^{-1}$ (C—H stretch), 1259 cm-1 and 1232 $cm^{-1}$ (doublet, asymmetric stretch of the $SO_2$ group of secondary alkyl sulfate salt), 1051 $cm^{-1}$ (symmetric stretch of the $SO_2$ group), 1026 $cm^{-1}$ (C—O stretch), and 843 $cm^{-1}$ (asymmetric stretch of the S—O—C). The presence of glucuronic acid in the side chain of FUC gave a characteristic band at 1638 $cm^{-1}$ (asymmetric stretch of $CO_2$). In the (+)- and (−)-FUC-HTCC NPs, the 1259 $cm^{-1}$ peak of asymmetric $SO_2$ stretching shifted to 1256 and 1255 $cm^{-1}$, respectively, and the 1051 $cm^{-1}$ peak of symmetric $SO_2$ stretching shifted to 1054 $cm^{-1}$. These differences indicated that polyelectrolyte complexation (PEC) occurred intermolecularly between the quaternary ammonium group of HTCC and the sulfate groups of FUC.

Figure 5C:
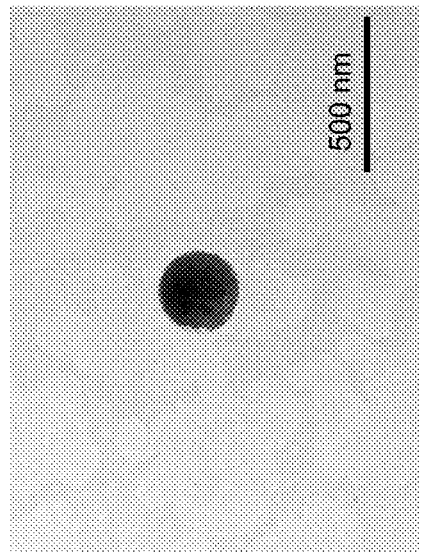
Figure 5B:
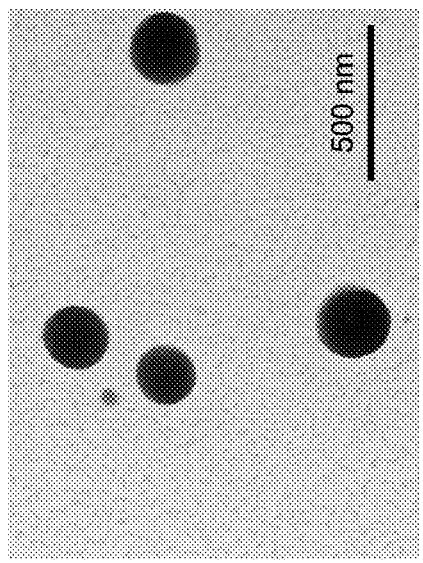

Representative TEM images of re-suspended (+)-FUC-HTCC NPs and (−)-FUC-HTCC NPs are shown in FIG. 5B and FIG. 5C, respectively. These images show a uniform, well-defined, and round structure for both types of charged FUC-HTCC NPs, consistent with the particle sizes measured via dynamic light scattering. The TEM images also indicate that both charged NPs could re-suspend well in solution with comparable size after centrifugal purification.

b. Characterization of FUC-TMCC NPs

Figure 6A:
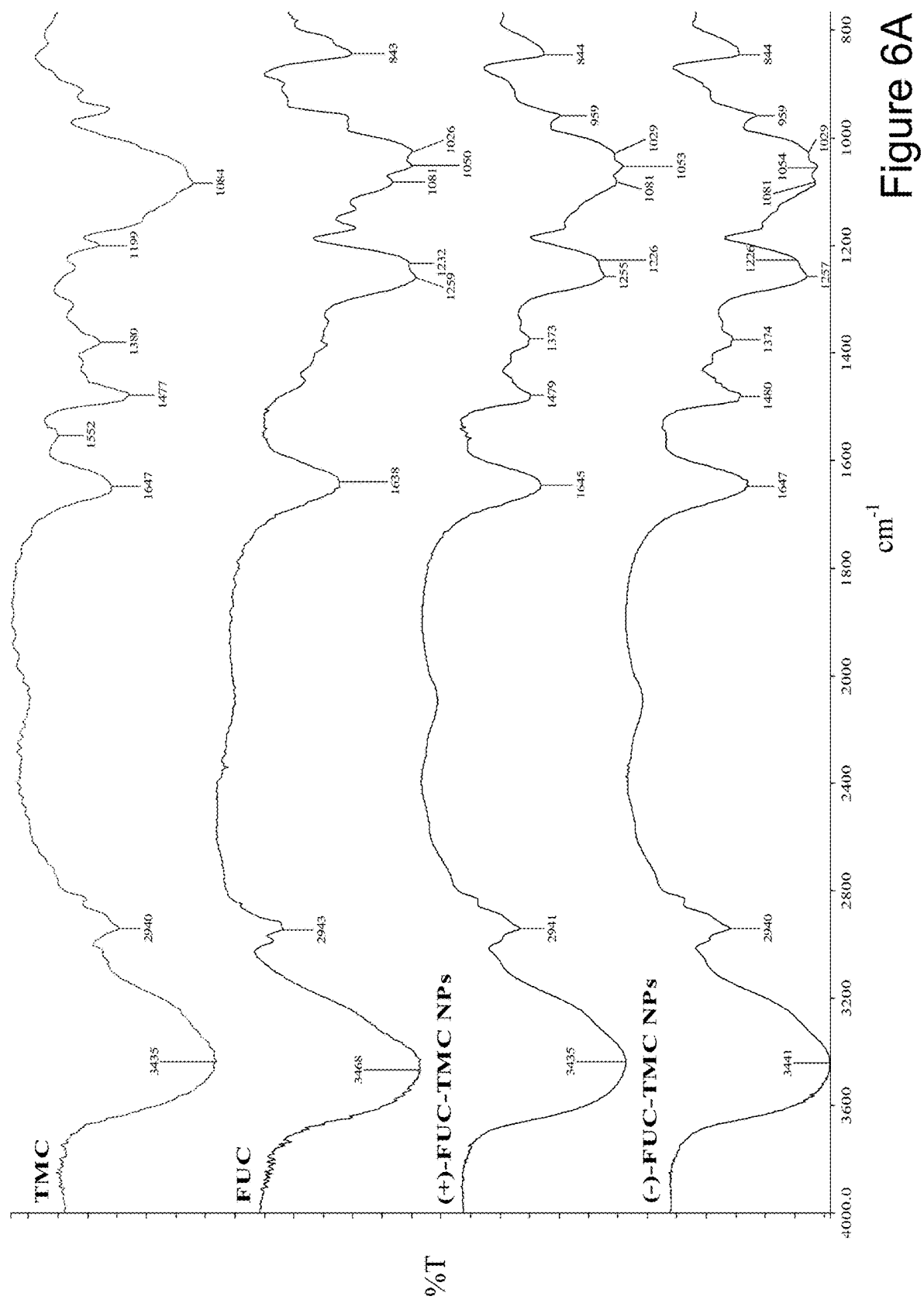
FIGS. 6A-C show the characteristics of fucoidan-N,N,N-Trimethyl chitosan chloride nanoparticles (FUC-TMCC NPs): Fourier transform infrared spectra of TMCC, FUC, (+)-FUC-TMCC NPs, and (−)-FUC-TMCC NPs (FIG. 6A), and transmission electron microscopy imaging of re-suspended (+)-FUC-TMCC NPs (FIG. 6B) and (−)-FUC-TMCC NPs (FIG. 6C) after centrifugal purification.

In FIG. 6A, the FTIR spectrum of FUC contains characteristic peaks at 3468 $cm^{-1}$ (O—H stretch), 2943 $cm^{-1}$ (C—H stretch), 1259 cm-1 and 1232 $cm^{-1}$ (doublet, asymmetric stretch of the $SO_2$ group of secondary alkyl sulfate salt), 1051 $cm^{-1}$ (symmetric stretch of the $SO_2$ group), 1026 $cm^{-1}$ (C—O stretch), and 843 $cm^{-1}$ (asymmetric stretch of the S—O—C). The presence of glucuronic acid in the side chain of FUC gave a characteristic band at 1638 $cm^{-1}$ (asymmetric stretch of $CO_2$). In the (+)- and (−)-FUC-TMCC NPs, the 1259 $cm^{-1}$ peak of asymmetric $SO_2$ stretching shifted to 1255 and 1257 $cm^{-1}$, respectively, and the 1050 $cm^{-1}$ peak of symmetric $SO_2$ stretching shifted to 1053 and 1054 $cm^{-1}$, respectively. These differences indicated that polyelectrolyte complexation (PEC) occurred intermolecularly between the quaternary ammonium group of TMCC and the sulfate groups of FUC.

Figure 6C:
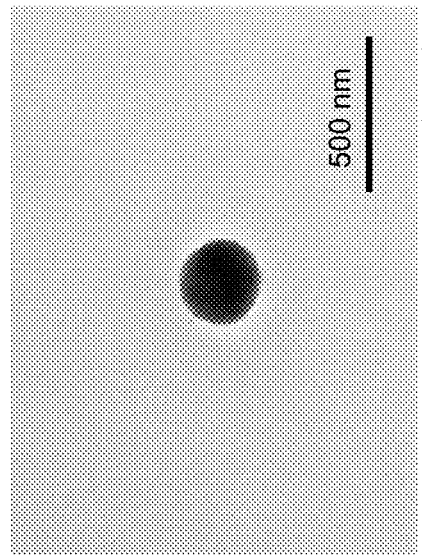
Figure 6B:
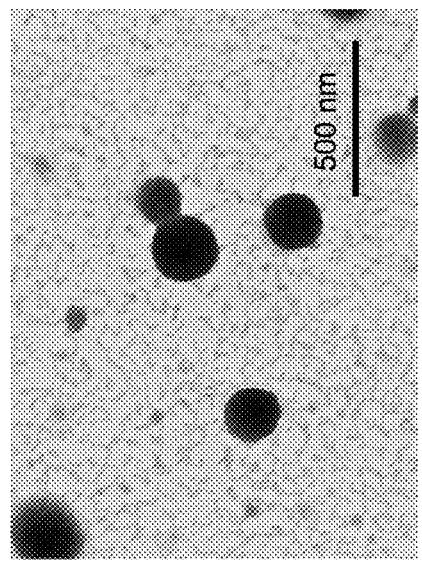

Representative TEM images of re-suspended (+)-FUC-TMCC NPs and (−)-FUC-TMCC NPs are shown in FIGS. 6B and 6C, respectively. These images show a uniform, well-defined, and round structure for both types of charged FUC-TMCC NPs, consistent with the particle sizes measured via dynamic light scattering. The TEM images also indicate that both charged NPs could re-suspend well in solution with comparable size after centrifugal purification.

Example 4

Cytotoxicity Assays of fucoidan-N-[(2-hydroxy-3-trimethyl-ammonium)propyl]chitosan chloride nanoparticles (FUC-HTCC NPs) and fucoidan-N,N,N-Trimethylchitosan chloride nanoparticles (FUC-TMCC NPs)

1. Cell Culture

L929 mouse fibroblast cells were obtained from American Type Culture Collection (ATCC; Rockville, Md., USA). Cells were seeded onto multi-well tissue culture plates, fed with DMEM, supplemented with 10% FBS and incubated at 37° C. in a 5% $CO_2$ environment.

The JAWS II DC line (ATCC) is an immortalized and immature dendritic cell line derived from bone marrow of C57BL/6 mice. The cells were maintained in Alpha-modified minimum essential medium (α-MEM; Sigma, St Louis, Mo. USA) supplemented with 20% FBS, 4 mM L-glutamine, 100 U/mL penicillin, 100 μg/mL streptomycin, 50 μg/mL gentamicin (Invitrogen, Grand Island, N.Y., USA) and 5 ng/mL of recombinant murine granulocyte macrophage colony-stimulating factor (GM-CSF; PeproTech, Rocky Hill, N.J., USA).

2. Cell Viability Assay

Cell viability was evaluated using an MTT (3-(4,5-dimethylthiazolyl-2)-2,5-diphenyl tetrazolium bromide) assay and performed according to the manufacturer's protocol. Briefly, L929 cells were seeded onto 96-well plates (Corning) at a density of 3000 cells per well in DMEM and cultured in a $CO_2$ incubator at 37° C. for 24 h. The medium was replaced by different DMEM solutions containing either FUC, HTCC, FUC-HTCC NPs, TMCC, or FUC-TMCC NPs in different concentrations (0, 3.125, 6.25, 12.5, 25, 50, 100, 200, and 400 μg/mL) and the cells were incubated in these solutions for 24 hours. After incubation, 10 μL MTT reagent was added to the cells. During an additional incubation time of 3 hours, MTT was converted by the living cells. The metabolic product formazan was solubilized by replacing the MTT-containing medium against 200 μL dimethyl sulfoxide. After mixing, the optical density was recorded at 570 nm using a Multiskan EX ELISA reader (Thermo Scientific). For each concentration, triplets were performed to determine the standard deviation.

Results

Figure 7A:
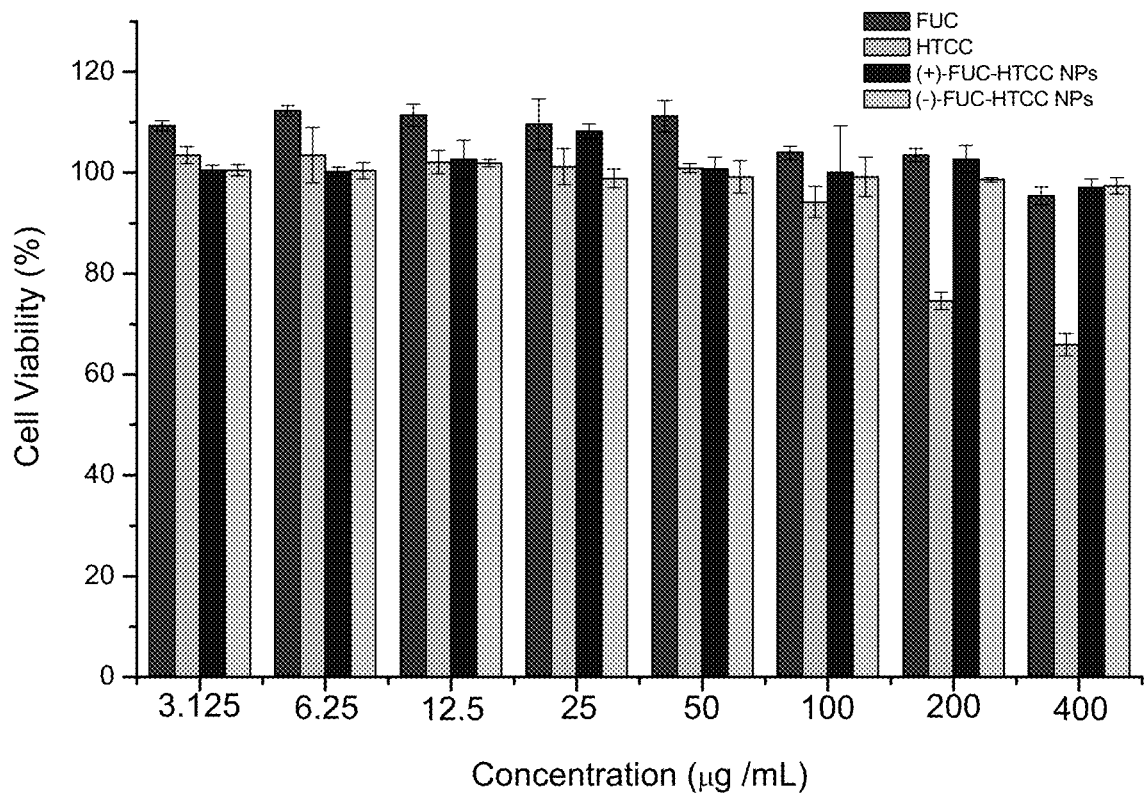
FIG. 7A shows cell viability of fucoidan (FUC), HTCC, (+)-FUC-HTCC NPs, and (−)-FUC-HTCC NPs on L929 cells at different concentrations measured by MTT assay.
Figure 8A:
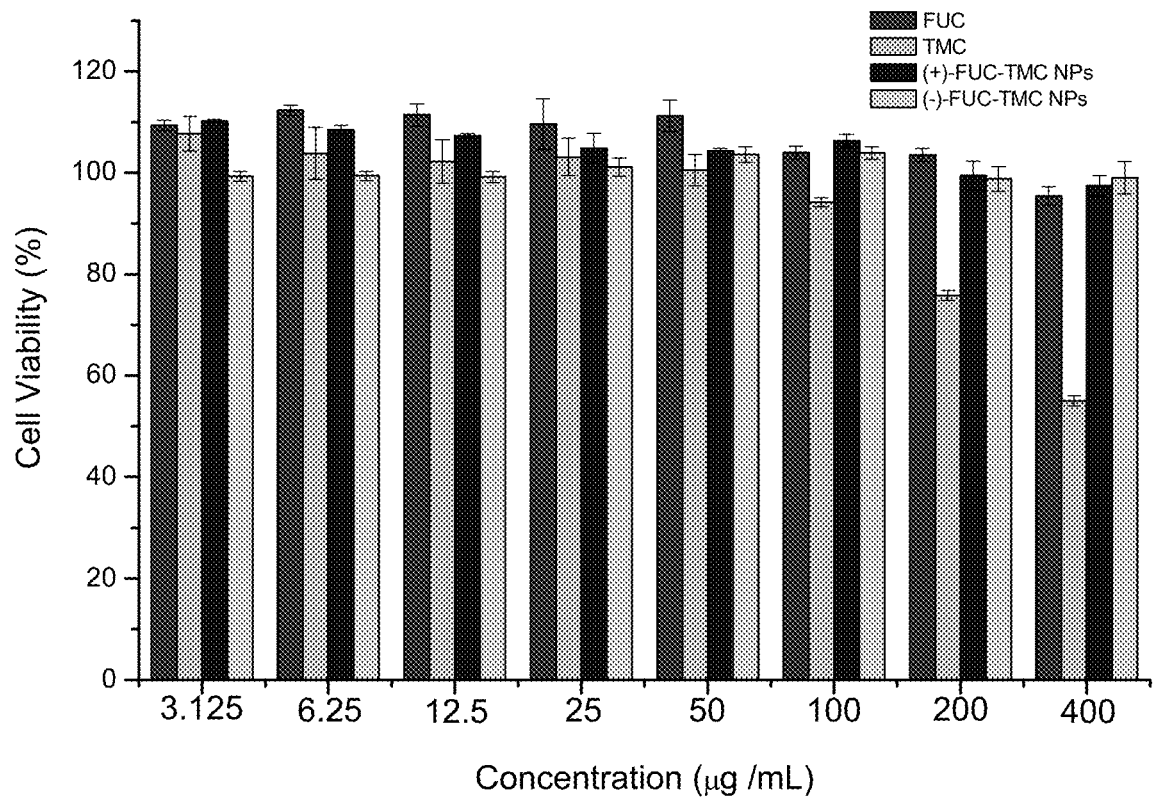
FIG. 8A shows cell viability of fucoidan (FUC), TMCC, (+)-FUC-TMCC NPs, and (−)-FUC-TMCC NPs on L929 cells at different concentrations measured by MTT assay.

For the assessment of cell viability, L929 cells were incubated with FUC, HTCC, (+)-FUC-HTCC NPs, (−)-FUC-HTCC NPs, TMCC, (+)-FUC-TMCC NPs, or (−)-FUC-TMCC NPs at various concentrations for 24 hours. FIG. 7A shows that over 95% of the cells were viable after incubation with FUC, (+)-FUC-HTCC NPs, and (−)-FUC-HTCC NPs at concentrations of 400 μg/mL or below, whereas in the case of HTCC, the cell viability was less than 73% at concentrations larger than or equal to 200 μg/mL. Similarly, FIG. 8A shows that over 95% of the cells were viable after incubation with FUC, (+)-FUC-TMCC NPs, and (−)-FUC-TMCC NPs at concentrations of 400 μg/mL or below, whereas in the case of TMCC, the cell viability was less than 75% at concentrations larger than or equal to 200 μg/mL.

3. Cytotoxicity Assay

Cytotoxicity was evaluated by the quantification of plasma membrane damage based on the measurement of lactate dehydrogenase (LDH), a stable cytoplasmic enzyme, released from damaged cells. The working solutions and assay method were performed according to the manufacturer's protocol. In brief, JAWS II DCs were seeded in 24-well plates ($1\times10^5$ cells/well) and incubated overnight. Then, the culture medium was removed and 400 pt of medium containing 0, 25, 50, 100, 200, and 400 µg/mL of FUC, HTCC, FUC-HTCC NPs, TMCC, or FUC-TMCC NPs and 1% FBS were added. After 24 hours of incubation, the plates were centrifuged at 250 xg and 4° C. for 10 minutes. The relative amounts of dead and live cells within the medium can be quantitated using LDH Cytotoxicity Detection Kit (BioVision, Calif., USA). The tetrazolium salt (INT) was converted to red formazan by LDH, and the amount of formazan was recorded at 490 nm wavelength (reference wavelength is 600 nm) using a Quant Microplate Spectrophotometer (BioTek Instruments Inc., Winooski, Vt., USA). Cells treated with medium which containing 1% Triton X-100 was used as high control (100% cytotoxicity). Cytotoxicity was calculated by the following equation:

Cytotoxicity (%)=$([A]_s-[A]_m)/([A]_h-[A]_m)\times100$ where $[A]_s$, $[A]_m$, and $[A]_h$ denote the absorbance of the sample, medium control and high control, respectively. All experiments were performed in triplicate.

Results

Figure 7B:
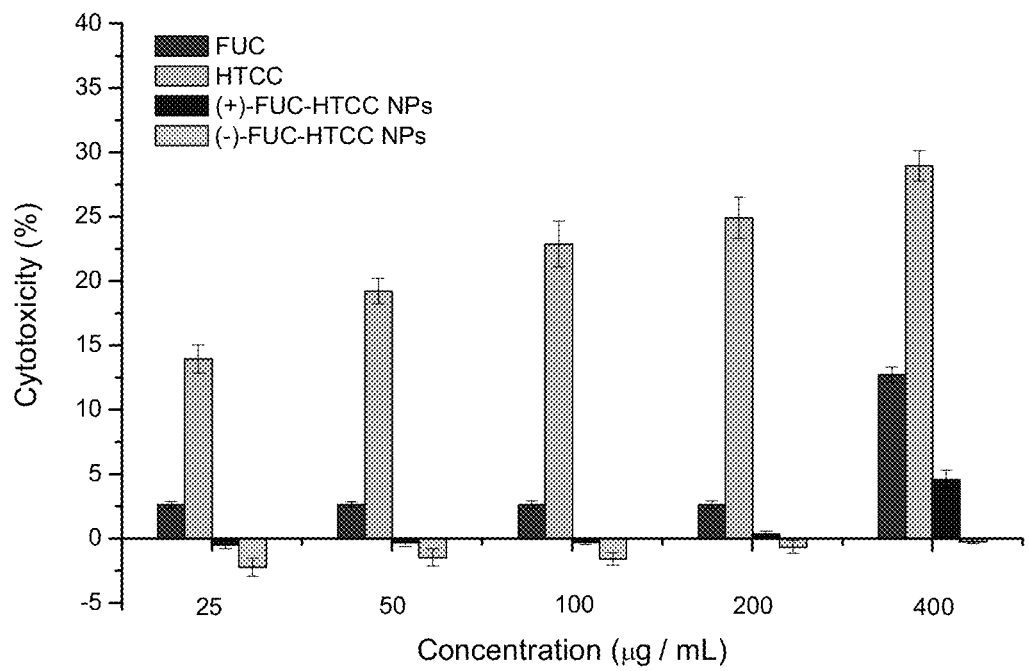
FIG. 7B shows cytotoxicity of fucoidan (FUC), HTCC, (+)-FUC-HTCC NPs, and (−)-FUC-HTCC NPs on JAWS II DCs at different concentrations measured by LDH release assay.
Figure 8B:
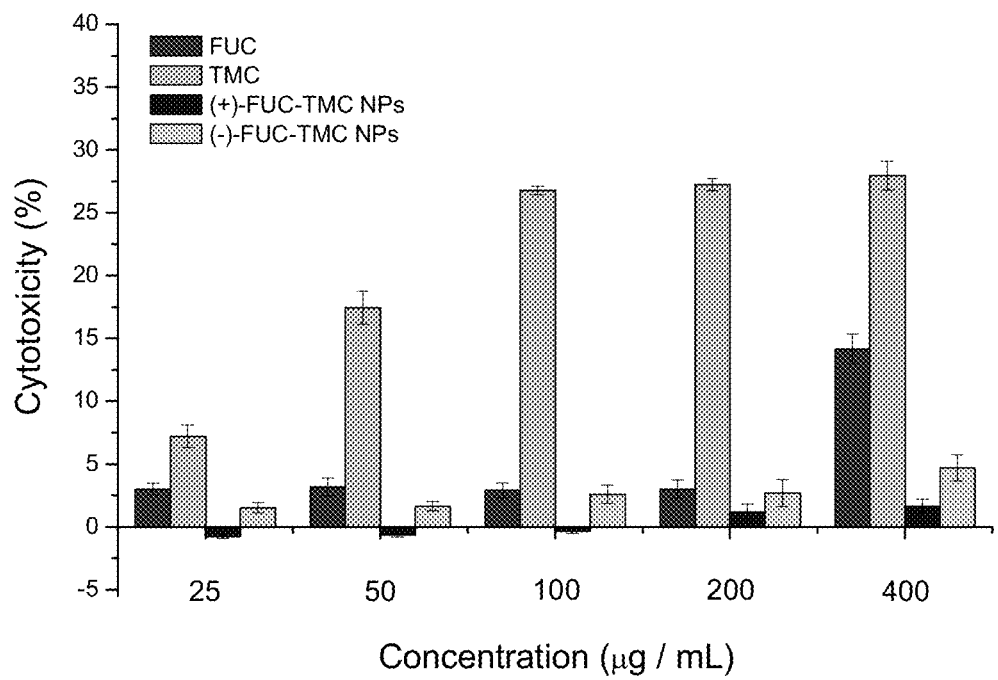
FIG. 8B shows cytotoxicity of fucoidan (FUC), TMCC, (+)-FUC-TMCC NPs, and (−)-FUC-TMCC NPs on JAWS II DCs at different concentrations measured by LDH release assay.

The results of the LDH assays of FUC-HTCC NPs and FUC-TMCC NPs are shown in FIG. 7B and FIG. 8B, respectively. FIG. 7B shows that 1429% of JAWS II DCs were injured at various concentrations of HTCC (25400 µ/mL). Similarly, FUC also showed some cytotoxicity (about 13%) on JAWS II cells at a concentration of 400 µg/mL. In contrast, even at very high total polysaccharide concentration (TPC) (400 µg/mL) of NPs, both (+)-FUC-HTCC NPs and (−)-FUC-HTCC NPs showed no plasma membrane damage based on their lactate dehydrogenase measurement.

FIG. 8B shows that about 1728% of JAWS II DCs were injured at various concentrations of TMCC (50400 µg/mL). In contrast, even at very high total polysaccharide concentration (TPC) (400 µ/mL) of NPs, both (+)-FUC-TMCC NPs and (−)-FUC-TMCC NPs showed no plasma membrane damage based on their lactate dehydrogenase measurement.

Our data indicated that even though FUC, HTCC, and TMCC showed some cytotoxicity in L929 cells and JAWS II DCs, (+)-FUC-HTCC NPs, (−)-FUC-HTCC NPs, (+)-FUC-TMCC NPs, and (−)-FUC-TMCC NPs still possess and show high cyto-compatibility in L929 cells and JAWS II DCs assessed via either cell viability or cytotoxicity assays. Thus, NP formation reduced the cytotoxicity of the original composites in the formula of the present invention. These results indicated that (+)-FUC-HTCC NPs, (−)-FUC-HTCC NPs, (+)-FUC-TMCC NPs, and (−)-FUC-TMCC NPs are safer and more suitable than FUC, HTCC, and TMCC as drug carriers or vaccine adjuvants, especially when a high dose is needed.

Example 5

Preparation of fucoidan-fluorescein 5(6)-isothiocyanate-conjugated N-[(2-hydroxy-3-trimethyl-ammonium)-propyl]chitosan chloride nanoparticles (FUC-f-HTCC NPs)

Step 1-A: Synthesis of fluorescein 5(6)-isothiocyanate-conjugated N-(2-hydroxy)propyl-3-trimethyl ammonium chitosan chloride (FITC-conjugated HTCC, f-HTCC)

The HTCC obtained from Step 1-1 of Example 1 was dissolved in milli-Q water. A solution of fluorescein 5(6)-isothiocyanate (FITC) (Sigma-Aldrich, St. Louis, Mo., USA) in dimethyl sulfoxide (DMSO) (Merck, Darmstadt, Germany) was slowly added to an aqueous solution of HTCC while stirring continuously. The reaction was carried out overnight at room temperature in the dark. The resulting solution was protected from light and dialyzed against water using a Dialysis Cassette (Slide-A-Lyzer® G2, 2000 MWCO) for 4 days. The dialyzed solution was then lyophilized and stored in the dark at −20° C. To determine the labeling efficiency, a specified amount of the f-HTCC was dissolved in milli-Q water and the absorbance intensity was measured using an ELISA Reader (Multiskan EX, Thermo, Finland) at 450 nm (data not shown). In these studies, freshly prepared FITC standard solutions were used to create a calibration curve for analysis.

Step 1-B: Preparation of fucoidan-fluorescein 5(6)-isothiocyanate-conjugated N-[(2-hydroxy-3-trimethyl-ammonium)-propyl]chitosan chloride nanoparticles (FUC-f-HTCC NPs)

Positively (+) and negatively surface-charged (−)-FUC-f-HTCC NPs were prepared via PEC by mixing anionic polyelectrolyte FUC (from *Fucus vesiculosus*) with cationic polyelectrolyte f-HTCC (product of Step 1-A) at a FUC/HTCC weight ratio of 0.82 and 1.22, respectively, with a TPC of 4 mg/mL. The fluorescent FUC-f-HTCC was used to further detect the cellular uptake of NPs.

Example 6

Preparation of fucoidan-fluorescein 5(6)-isothiocyanate-conjugated N,N,N-Trimethyl chitosan chloride nanoparticles (FUC-f-TMCC NPs)

Step 2-A: Synthesis of fluorescein 5(6)-isothiocyanate-conjugated N,N,N-Trimethyl chloride chitosan (FITC-conjugated TMCC, f-TMCC)

FITC dissolved in dimethyl sulfoxide was slowly added to the TMCC aqueous solution obtained from Step 2-1 of Example 2 under continuous stirring. The reaction was carried out overnight at room temperature in the dark. The resulting solution was poured into an excess of acetone and centrifuged for 10 minutes at 3000 rpm. The pellet was washed several times with fresh acetone until no FITC fluorescence was observed in the washing solution. The pellet was then dissolved in water and dialyzed against water with a dialysis cassette (Slide-A-Lyzer®, G2, 2000 MWCO, 70-mL capacity) for 3 days while protected from light. The f-TMCC was then lyophilized. To determine the labeling efficiency, a specified amount of f-TMCC was dissolved in ultrapure water and measured the fluorescence intensity with a spectrofluorometer (Fluoroskan Ascent, Thermo, Finland) at $\lambda_{exe}$ 485 nm and $\lambda_{emi}$ 520 nm. The spectrofluorometer was calibrated with standard solutions of 0.0625-1 mg/mL FITC in the same solution (data not shown).

Step 2-B: Preparation of fucoidan-fluorescein 5(6)-isothiocyanate-conjugated N,N,N-Trimethyl chitosan chloride nanoparticles (FUC-f-TMCC NPs)

Positively (+) and negatively surface-charged (−)-FUC-f-TMCC NPs were prepared via PEC by mixing anionic polyelectrolyte FUC (from *Fucus vesiculosus*) with cationic polyelectrolyte f-TMCC (product of Step 2-A) at a FUC/TMCC weight ratio of 0.67 and 1.1, respectively, with a TPC of 4 mg/mL. The fluorescent FUC-f-TMCC was used to further detect the uptake of NPs by cells.

Example 7

Cellular Uptake Assays of fucoidan-fluorescein 5(6)-isothiocyanate-conjugated N-[(2-hydroxy-3-trimethyl-ammonium)-pr opyl] chitosan chloride nanoparticles (FUC-f-HTCC NPs) and fucoidan-fluorescein 5(6)-isothiocyanate-conjugated N,N,N-Trimethyl chitosan chloride nanoparticles (FUC-f-TMCC NPs)

1. Flow cytometric measurements of uptake of FUC-f-HTCC NP and FUC-f-TMCC NP by JAWS II DCs To determine NP uptake by the cells quantitatively, JAWS II DCs were cultured in 6-well cell culture plates ($1 \times 10^6$ cells/well) and incubated with FUC-f-HTCC NPs (product of Example 5) or FUC-f-TMCC NPs (product of Example 6) at TPC concentrations of 0.25, 1, and 4 μg/mL in a 5% $CO_2$ environment at 37° C. for 16 hours. Cells were dissociated from the plate using 0.25% trypsin and then washed three times with cold phosphate buffered saline (PBS) containing 1% fetal calf serum (FCS). A final wash was performed, and the cells were resuspended in 1% FCS/PBS. Data acquisition using CytoFLEX flow cytometer (Beckman Coulter Inc., Brea, Calif., USA) and flow cytometric compensation was performed using fluorescent compensation beads (VersaComp Antibody Capture Beads, Beckman Coulter Inc.). Data were analyzed using FlowJo 10.0.7 R2 software (Tree Star, Ashland, Oreg., USA). A flow cytometer was used to analyze 10,000 events for each sample, where untreated cells were used as negative controls.

Results

Figure 9A:
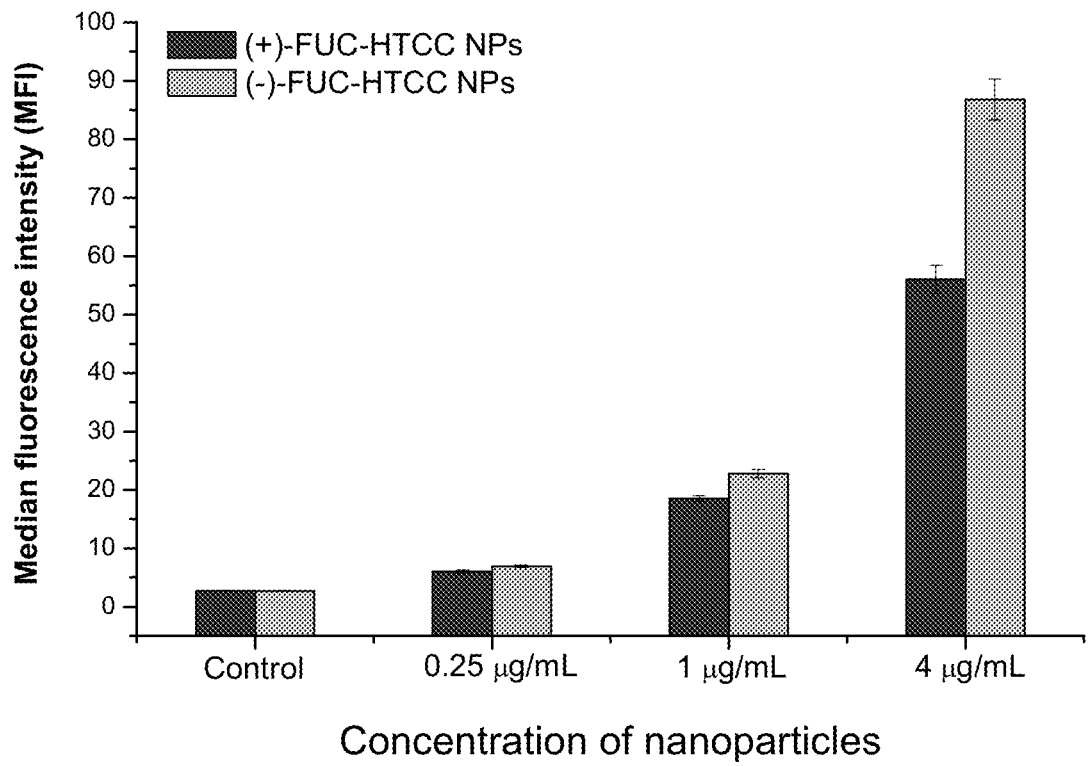
FIG. 9A shows median fluorescence intensity (MFI) measured at different concentrations of (+)-FUC-f-HTCC NPs and (−)-FUC-f-HTCC NPs for 16 hours.
Figure 9B:
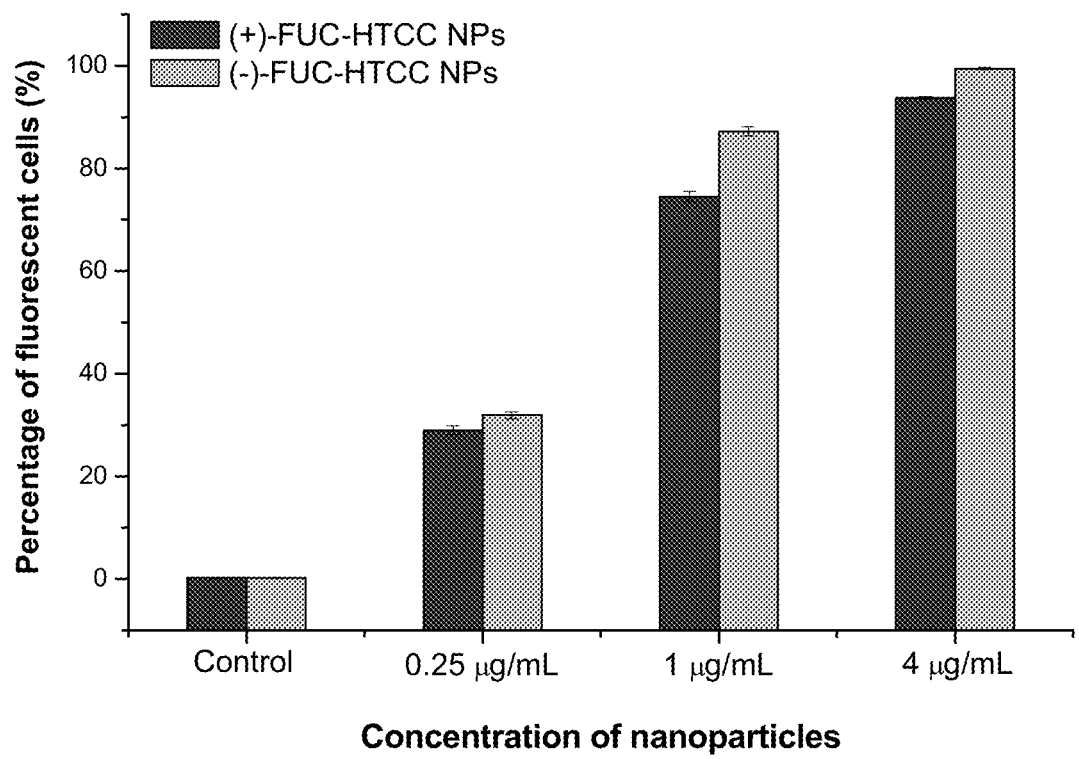
FIG. 9B shows percentage of fluorescence positive cells (%) measured at different concentrations of (+)-FUC-f-HTCC NPs and (−)-FUC-f-HTCC NPs for 16 hours.
Figure 10A:
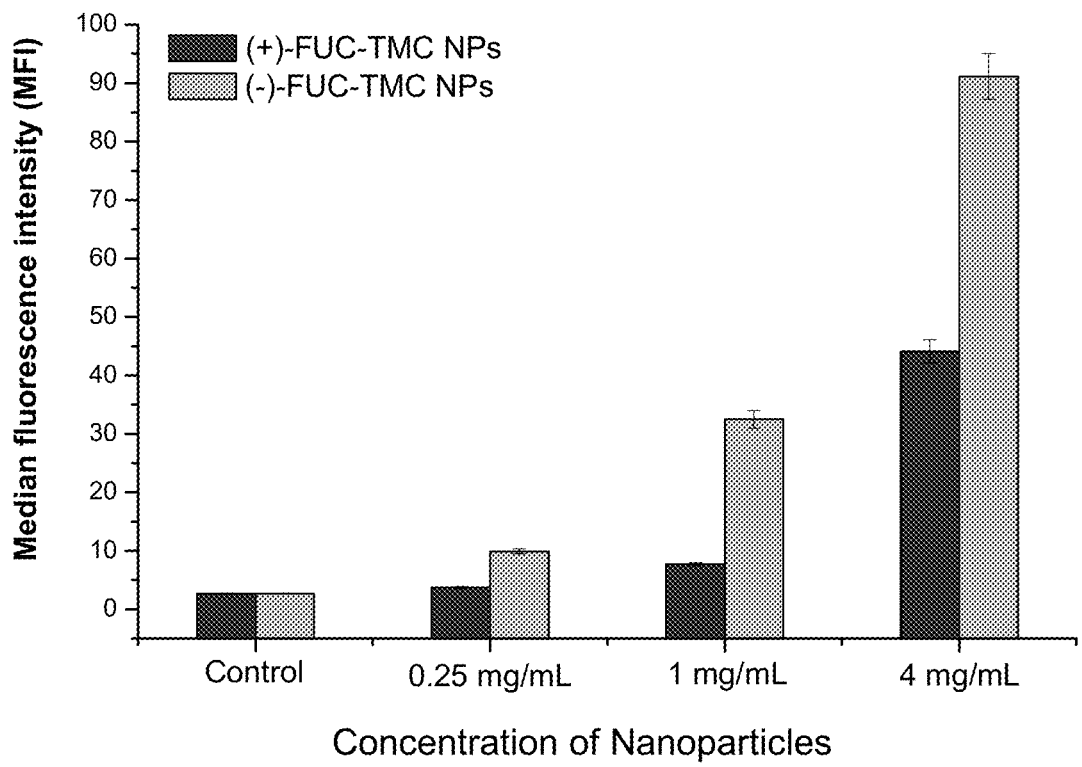
FIG. 10A shows median fluorescence intensity (MFI) measured at different concentrations of (+)-FUC-f-TMCC NPs and (−)-FUC-f-TMCC NPs for 16 hours.
Figure 10B:
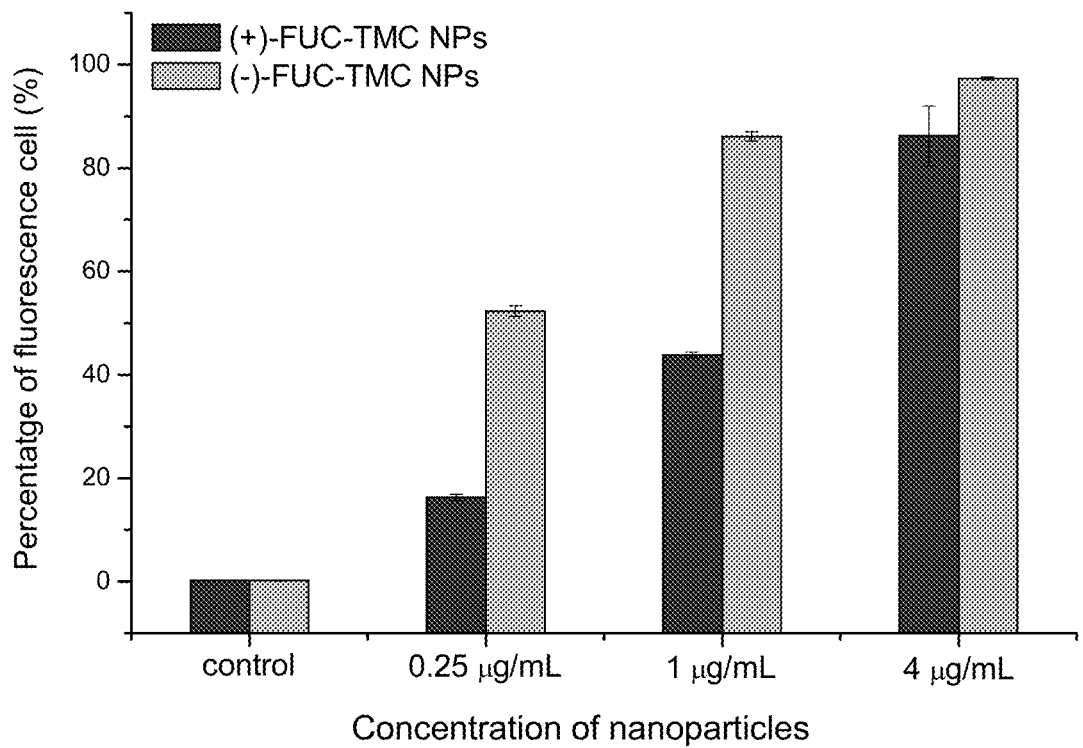
FIG. 10B shows percentage of fluorescence positive cells (%) measured at different concentrations of (+)-FUC-f-TMCC NPs and (−)-FUC-f-TMCC NPs for 16 hours.

The results of the flow cytometric analysis of FUC-f-HTCC NPs and FUC-f-TMCC NPs are shown in FIG. 9 and FIG. 10, respectively. The effect of concentration of (+)-FUC-f-HTCC NPs, (−)-FUC-f-HTCC NPs, (+)-FUC-f-TMCC NPs, and (−)-FUC-f-TMCC NPs on the median fluorescence intensity (MFI) and the percentages of fluorescent cells (%) are displayed in FIGS. 9A, 9B, 10A, and 10B, respectively. The data clearly demonstrate that NPs with negative charge (i.e., (−)-FUC-f-HTCC NPs and (−)-FUC-f-TMCC NPs) were internalized more abundantly than NPs with positive charge (i.e., (+)-FUC-f-HTCC NPs and (+)-FUC-f-TMCC NPs) by JAWS II DCs at all concentrations after incubation for 16 hours. Although NPs with negative charge (i.e., (−)-FUC-f-HTCC NPs and (−)-FUC-f-TMCC NPs) showed a slightly higher cellular uptake ability than NPs with positive charge (i.e., (+)-FUC-f-HTCC NPs and (+)-FUC-f-TMCC NPs), NPs with both charges showed excellent uptake efficacy by JAWS II DCs after incubation for a short period time at low concentrations (4 μg/mL). Over 93% of FUC-f-HTCC NPs were taken up by JAWS II DCs after being incubated with 4 μg/mL for 16 hours, and over 86% of FUC-f-TMCC NPs were taken up by JAWS II DCs after being incubated with 4 μg/mL for 16 hours. The results also indicate that the cellular uptake of NPs with both charges is proportional to the concentration of NPs in the media, which means in a dose dependent manner.

2. Fluorescence microscope images of uptake of FUC-f-HTCC NPs and FUC-f-TMCC NPs by JAWS II DCs To detect the uptake of NPs by cells qualitatively, JAWS II DCs were incubated with FUC-f-HTCC NPs (product of Example 5) or FUC-f-TMCC NPs (product of Example 6) at a TPC concentration of 4 μg/mL in a $CO_2$ incubator at 37° C. for 16 hours. Cells were washed three times with PBS and fixed in a 3.7% paraformaldehyde-PBS solution at room temperature for 10 minutes. After three additional washes with PBS, a sufficient amount of 300 nM of 4′,6-diamidino-2-phenylindole (DAPI) stain solution to submerge the cells was added at room temperature for 5 minutes and protected from light. Then, the stain solution was removed by washed three times with PBS. Finally, images were obtained using a BS-7000 series Fluorescent Microscope (Beijing BestScope Technology Co., Ltd.) and processed using SPOT software (SPOT Imaging, a division of Diagnostic Instruments, Inc.). Untreated cells were used as negative controls.

Results

Figure 11:
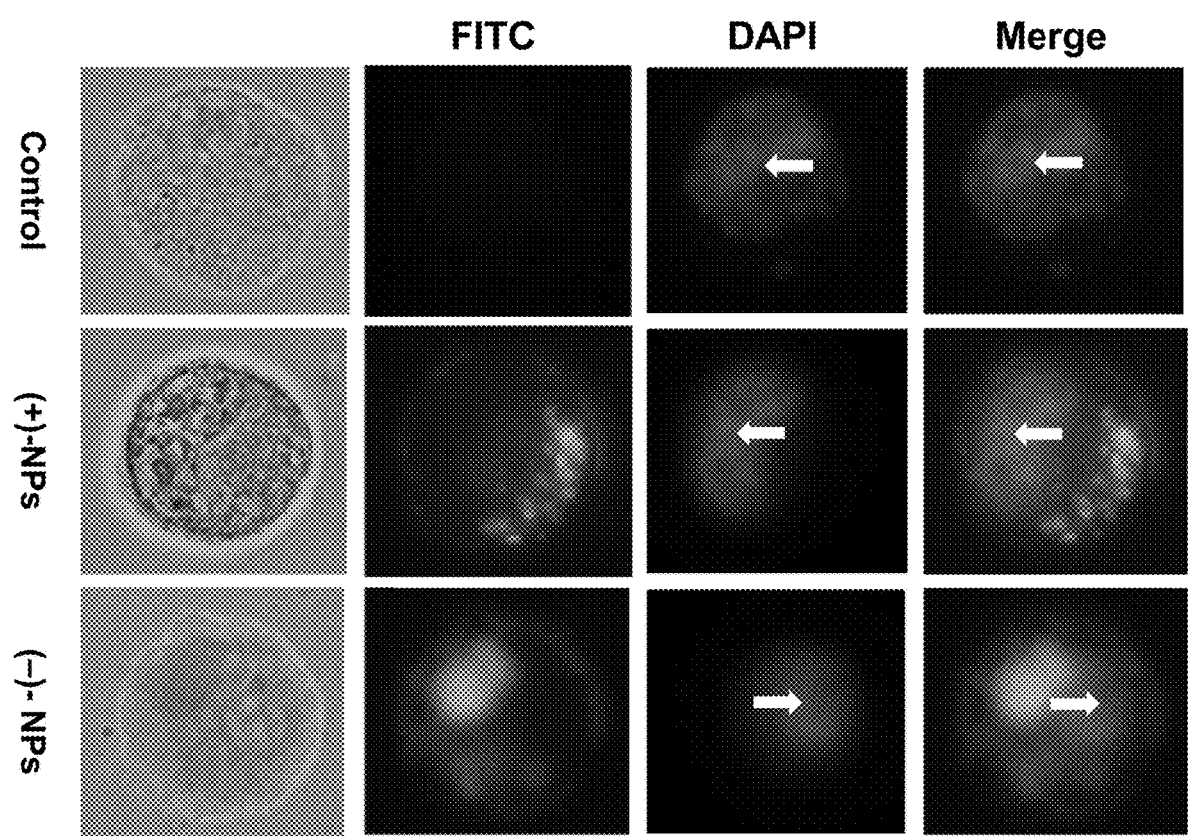
FIG. 11 shows fluorescence microscope images of JAWS II DCs after incubation with (+)-FUC-f-HTCC NPs or (−)-FUC-f-HTCC NPs for 16 hours. The cytoskeletons were stained with 4′,6-diamidino-2-phenylindole (DAPI), and the nuclei are indicated by arrows.
Figure 12:
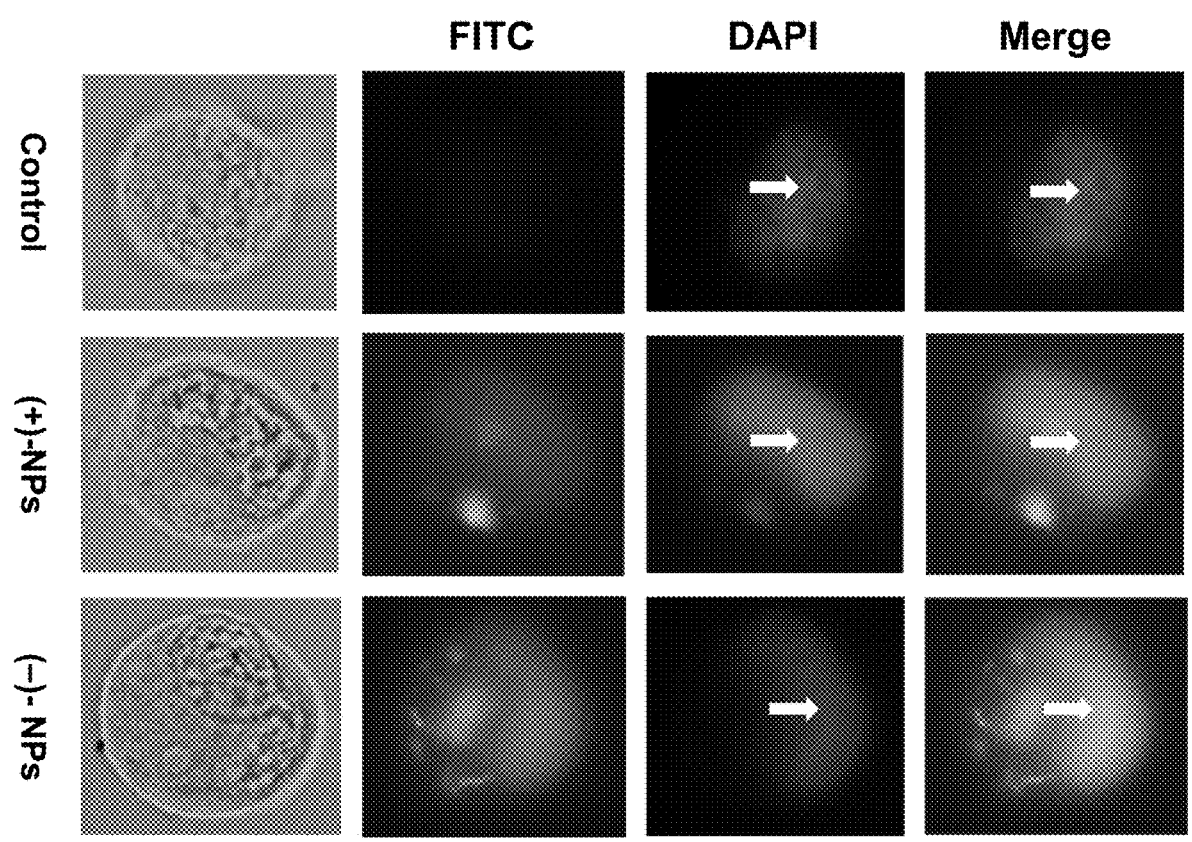
FIG. 12 shows fluorescence microscope images of JAWS II DCs after incubation with (+)-FUC-f-TMCC NPs or (−)-FUC-f-TMCC NPs for 16 hours. The cytoskeletons were stained with 4′,6-diamidino-2-phenylindole (DAPI), and the nuclei are indicated by arrows.

FIG. 11 and FIG. 12 show the fluorescence microscope images of JAWS II DCs after incubation with FUC-f-HTCC NPs and FUC-f-TMCC NPs for 16 hours, respectively. FIG. 11 shows that green fluorescence was retained within the cytoplasm of JAWS II DCs after incubation with (+)-FUC-f-HTCC NPs or (−)-FUC-f-HTCC NPs for 16 hours, which did not overlap with the nucleus (indicated by arrows). FIG. 12 shows that green fluorescence was retained within both of the cytoplasm and nucleus (indicated by arrows) of JAWS II DCs after incubation with (+)-FUC-f-TMCC NPs or (−)-FUC-f-TMCC NPs for 16 hours. The results clearly indicate that both FUC-HTCC NPs and FUC-TMCC NPs can enter cytoplasm of dendritic cells, and FUC-TMCC NPs with both charges can further enter nucleus of the cells, which implies a broader application as a carrier.

Example 8

Animal Testing

1. Immunization and challenge studies

To compare the efficacy of FUC-HTCC NPs, FUC-TMCC NPs, and CpG ODN as anthrax vaccine adsorbed (AVA) vaccine adjuvants in vivo, the following animal tests were conducted.

All animal studies were approved by the Institutional Animal Care and Use Committee (IACUC) of Institute of Preventive Medicine (IPM) of National Defense Medical Center (Taipei, Taiwan) and were conducted in AAALAC-accredited facilities. A/J mice were purchased from the Jackson Laboratories (Bar Harbor, Me., USA) and housed in sterile microisolator cages of the animal center of IPM in a barrier environment. Veterinarians monitored animals daily and the mice were bled weekly. The prime-boost strategy for immunization was adopted. Briefly, five groups of 4 female 6-8-week-old A/J mice were intraperitoneally (i.p.) immunized with a total volume in PBS of 500 μL, containing (1) 10 μL anthrax vaccine adsorbed (AVA) alone, (2) 10 μL AVA+20 μg CpG ODN, (3) 10 μL AVA+200 μg FUC, (4) 10 μL AVA+400 μg (+)-FUC-HTCC NPs, or (5) 10 μL AVA+400 μg (+)-FUC-TMCC NPs. All groups of mice were boosted 16 weeks post-priming. Sera were collected on 4, 6, 10, 16, 18, and 24 weeks post-priming for the serological analysis. Mice were i.p. challenged with anthrax lethal toxin (380 μg, 4 $LD_{50}$, LF:PA=15:85) in sterile PBS performed 8 weeks post-boosting. Survival was monitored for 21 days.

2. PA-specific antibody assay

IgG anti-protective antigen (PA) titers were measured by coating 96-well polystyrene microtiter plates with PA (500 ng/well) PBS solution at 4° C. overnight, then blocked by PBST (PBS containing 0.05% Tween-20), and washed three times with PBST. Sera obtained from mice were diluted serially. A 100 μL volume of diluted sera was added to each well of the microtiter plate in duplicate and incubated at room temperature for 1 hour, and then washed three times with PBST. Bound antibody was detected using horseradish peroxidase (HRP)-conjugated goat-anti mouse IgG (H+L) (Jackson ImmunoResearch, West Grove, Pa., USA) followed by TMB Peroxidase Substrate (SureBlue™, KPL Inc., Gaithersburg, Md., USA). The reaction was stopped by acidification using TMB stop solution. Finally, the solution absorbance was measured at 490 nm using μQuant Microplate Spectrophotometer (BioTek Instruments, Inc., Winooski, Vt., USA). Antibody titers were expressed as the reciprocal of the end point dilution.

Results

Figure 13:
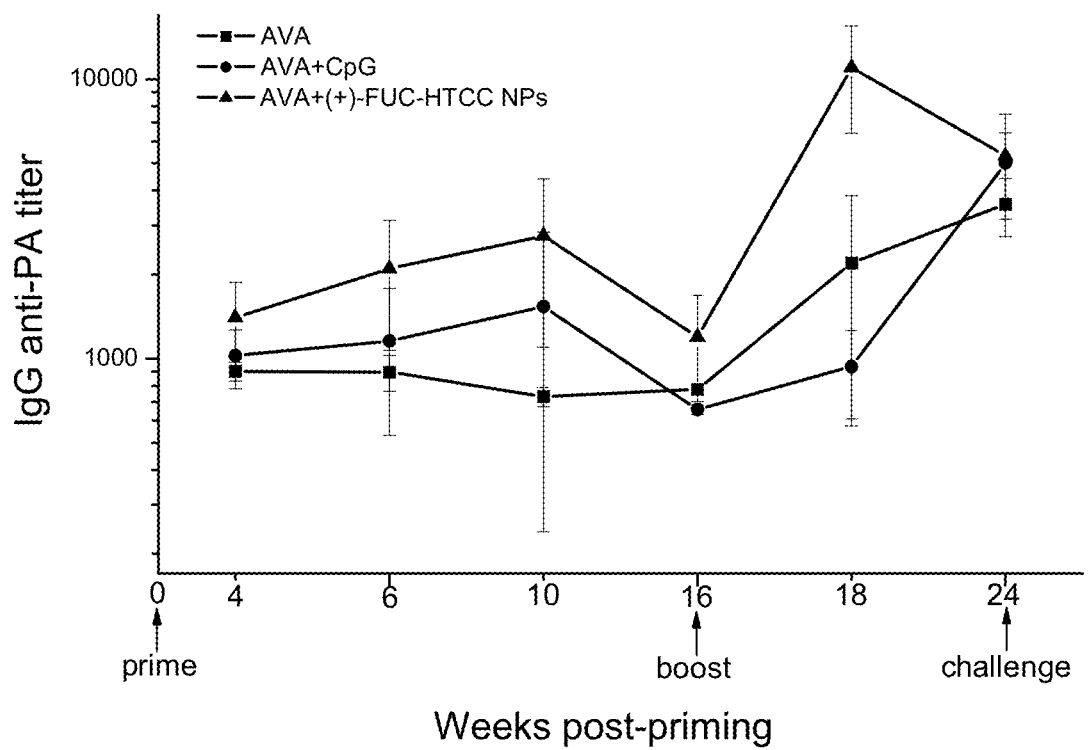
FIG. 13 shows protective antigen (PA)-specific IgG responses in A/J mice sera collected on weeks post-priming, following the immunization procedures with AVA (■), AVA+CpG (●), and AVA+(+)-FUC-HTCC NPs (▲), respectively. Error bars indicate standard deviation (SD).

FIG. 13 shows that both FUC-HTCC NPs and CpG ODN increase the productiveness of the IgG-anti-PA antibody response induced by AVA in A/J mice. Furthermore, AVA plus FUC-HTCC NPs induced higher IgG-anti-PA titers compared with AVA only and AVA plus CpG ODN during all the monitored periods. The IgG-anti-PA titers were found to increase rapidly at the beginning of the 10 weeks post-priming and 2 weeks post-boosting (18 weeks post-priming) when mice co-immunized with FUC-HTCC NPs.

Figure 14:
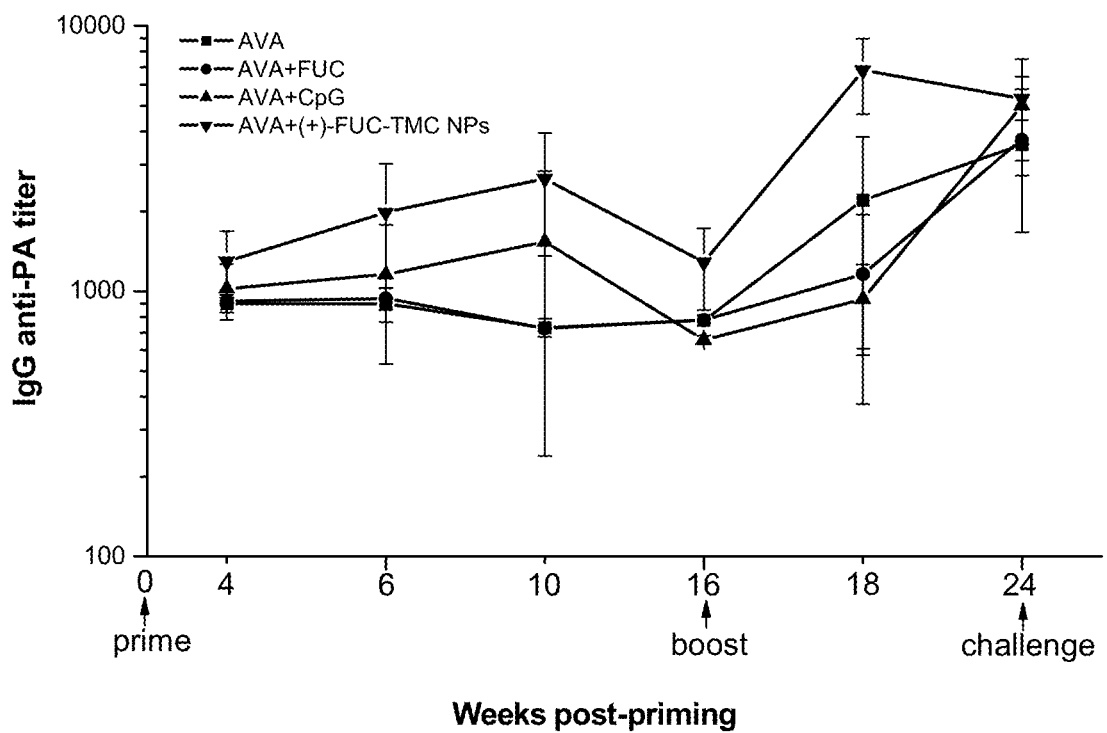
FIG. 14 shows protective antigen (PA)-specific IgG responses in A/J mice sera collected on weeks post-priming, following the immunization procedures with AVA (■), AVA+FUC (●), AVA+CpG (▲), and AVA+(+)-FUC-TMCC NPs (▼), respectively. Error bars indicate SD.

Similarly, FIG. 14 shows that AVA plus FUC-TMCC NPs induced higher IgG-anti-PA titers compared with AVA only, AVA plus FUC, and AVA plus CpG ODN during all the monitored periods. The IgG-anti-PA titers were found to increase rapidly at the beginning of the 10 weeks post-priming and 2 weeks post-boosting (18 weeks post-priming) when mice co-immunized with FUC-TMCC NPs.

Figure 15:
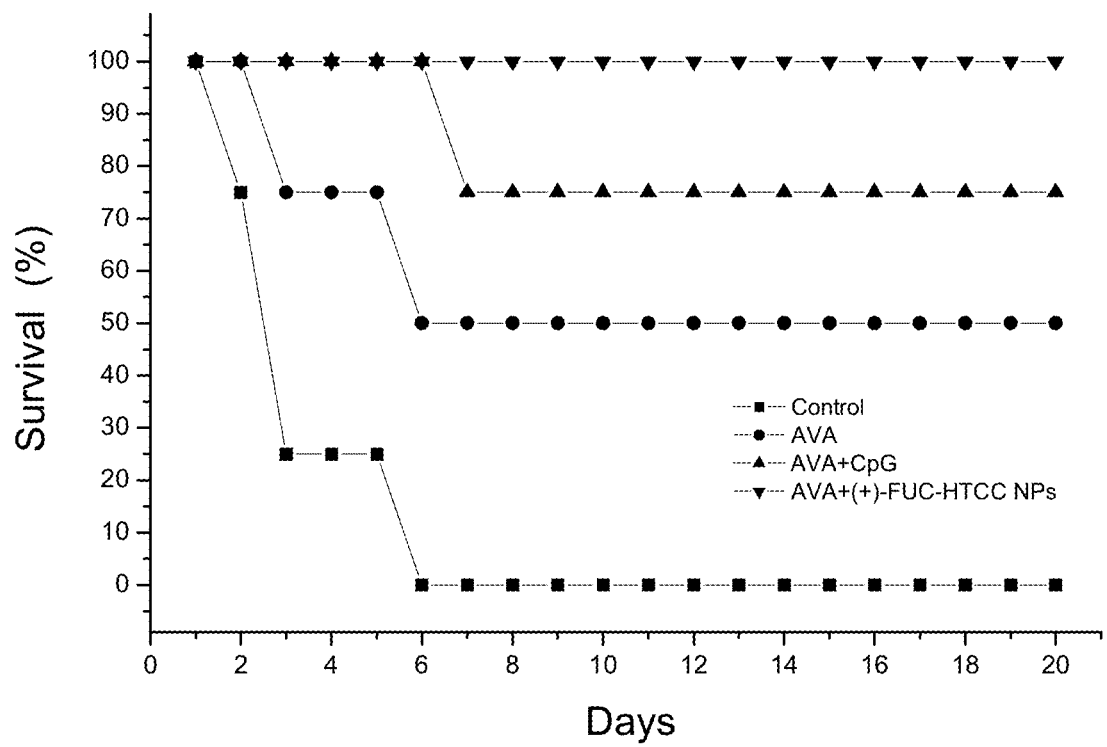
FIG. 15 shows protection of mice from an i.p. anthrax toxin challenge using (+)-FUC-HTCC NPs (▼) and CpG ODN (▲) as adjuvant of AVA or AVA alone (●) compared to negative control (■).
Figure 16:
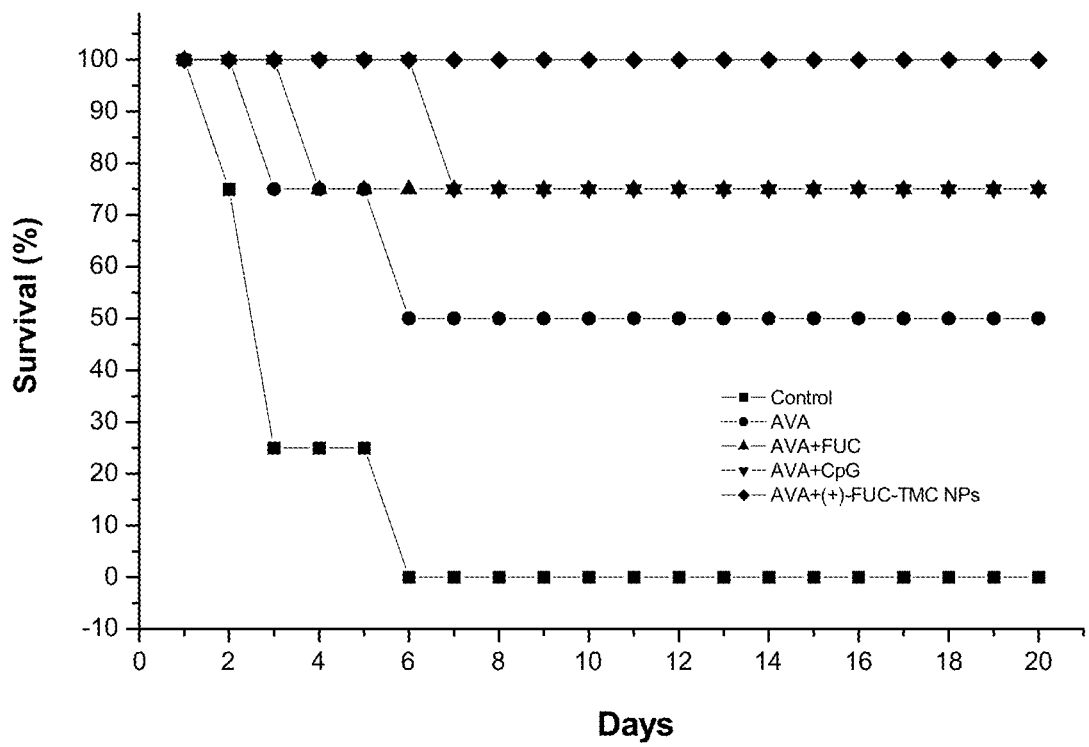
FIG. 16 shows protection of mice from an i.p. anthrax toxin challenge using FUC (▲), CpG ODN (▼) and (+)-FUC-TMCC NPs (♦) as adjuvant of AVA or AVA alone (●) compared to negative control (■).

To directly evaluate protection, vaccinated mice were challenged 8 weeks post-boosting (24 weeks post-priming) with 4 $LD_{50}$ of anthrax lethal toxin and the survival rates were monitored for 21 days. FIG. 15 shows that a greater ratio of mice immunized with AVA plus FUC-HTCC NPs (100% survival) survived compared to those immunized with AVA plus CpG ODN (75% survival), AVA alone (50% survival), or the control (0% survival within 6 days). Similarly, FIG. 16 shows that a greater ratio of mice immunized with AVA plus FUC-TMCC NPs (100% survival) survived compared to those immunized with AVA plus CpG ODN (75% survival), AVA plus FUC (75% survival), AVA alone (50% survival), or the control (0% survival within 6 days).

These results indicate that the combination of (+)-FUC-HTCC NPs plus AVA and the combination of (+)-FUC-TMCC NPs plus AVA trigger a faster, higher avidity, and a higher-titer IgG anti-PA antibody than CpG ODN plus AVA, FUC plus AVA, or AVA alone (FIGS. 13 and 14). Also, the addition of (+)-FUC-HTCC NPs or (+)-FUC-TMCC NPs to AVA significantly increased protection (100% survival) in A/J mice compared to CpG ODN plus AVA (75% survival) or AVA alone (50% survival) (FIGS. 15 and 16). It is worth noting that no serious local or systemic adverse reactions were observed in any of the A/J mice treated with (+)-FUC-HTCC NPs plus AVA or (+)-FUC-TMCC NPs.

In this Example, the inventors demonstrated that FUC-HTCC NPs and FUC-TMCC NPs are both good nano-carriers and vaccine adjuvant.

Many changes and modifications in the above described embodiment of the invention can, of course, be carried out without departing from the scope thereof. Accordingly, to promote the progress in science and the useful arts, the invention is disclosed and is intended to be limited only by the scope of the appended claims.

What is claimed is:

1. A fucoidan-quaternized chitosan nanoparticle as a vaccine adjuvant, consisting of:

10 to 90% by weight of anionic fucoidan as an anionic polyelectrolyte; and 90 to 10% by weight of cationic N,N,N-trimethyl chitosan chloride (TMCC) as a cationic polyelectrolyte, wherein the TMCC has a degree of quaternization (DQ) of 51%~200%.

2. The fucoidan-quaternized chitosan nanoparticle of claim 1, wherein the N,N,N-trimethyl chitosan chloride (TMCC) has a degree of deacetylation (DD) of 10%~99%.

3. The fucoidan-quaternized chitosan nanoparticle of claim 1, wherein the fucoidan-quaternized chitosan nanoparticle has a particle size of no more than about 1000 nm and an absolute value of zeta potential of no less than about 10 mV.

* * * * *